(12) United States Patent
Tyrrell et al.

(10) Patent No.: US 8,480,875 B2
(45) Date of Patent: Jul. 9, 2013

(54) APPARATUS, COMPOSITIONS AND METHODS FOR RAPID COMPETITIVE HOMOGENEOUS ASSAY

(75) Inventors: Steven Patrick Tyrrell, Erie, CO (US); Barry Vant-Hull, Boulder, CO (US)

(73) Assignee: Eveia Medical, Inc., Boulder, CO (US)

( * ) Notice: Subject to any disclaimer, the term of this patent is extended or adjusted under 35 U.S.C. 154(b) by 276 days.

(21) Appl. No.: 12/677,270

(22) PCT Filed: Sep. 10, 2008

(86) PCT No.: PCT/US2008/075894
§ 371 (c)(1),
(2), (4) Date: Apr. 12, 2011

(87) PCT Pub. No.: WO2009/036091
PCT Pub. Date: Mar. 19, 2009

(65) Prior Publication Data
US 2011/0180407 A1    Jul. 28, 2011

Related U.S. Application Data

(60) Provisional application No. 60/993,034, filed on Sep. 10, 2007, provisional application No. 60/995,186, filed on Sep. 25, 2007.

(51) Int. Cl.
*B01D 57/02*    (2006.01)

(52) U.S. Cl.
USPC .......... 204/618; 204/468; 204/456; 204/469

(58) Field of Classification Search
USPC ............... 204/450–470, 546–550, 600–621, 204/641–645
See application file for complete search history.

(56) References Cited

U.S. PATENT DOCUMENTS

| 5,958,202 A | 9/1999 | Regnier et al. | |
|---|---|---|---|
| 2005/0079519 A1* | 4/2005 | Boles et al. | 435/6 |
| 2007/0151853 A1* | 7/2007 | Beardslee et al. | 204/456 |
| 2008/0314751 A1* | 12/2008 | Bukshpan et al. | 204/466 |

OTHER PUBLICATIONS

International Search Report and Written Opinion dated Nov. 18, 2008, issued by the International Searching Authority in connection with counterpart international application No. PCT/US2008/075894.

* cited by examiner

*Primary Examiner* — Keith Hendricks
*Assistant Examiner* — Bach Dinh

(57) ABSTRACT

Embodiments herein concern systems, methods, compositions and apparatus for detection and/or determination of the presence and/or concentration of target molecules in a sample. In certain embodiments, target molecules can be separated and analyzed using non-gel electrophoresis technologies.

16 Claims, 18 Drawing Sheets

A.

B.

✚ Neutravidin  ⊗ Target protein  🗲 Biotin-polymer

⊻ Biotin-Ab  ✴ FITC-Target  ∿ Linear acrylamide

C.

D.

A.                B.                C.

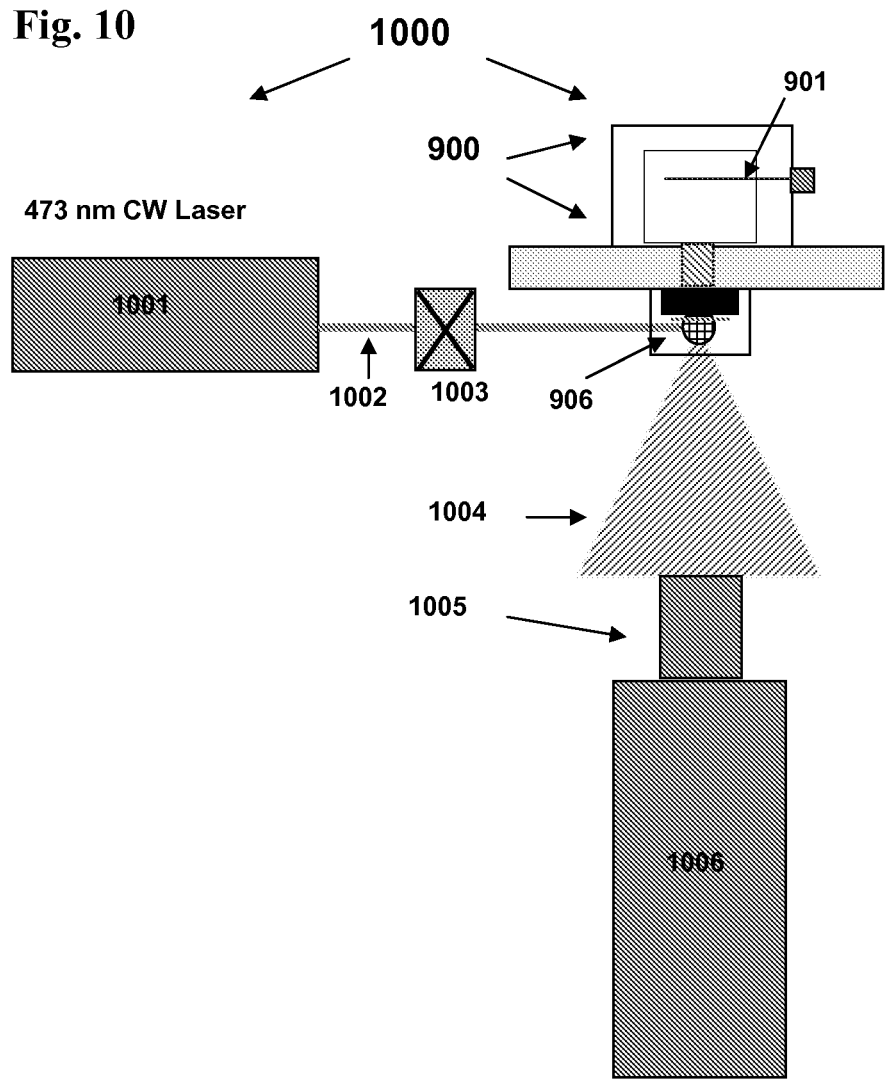

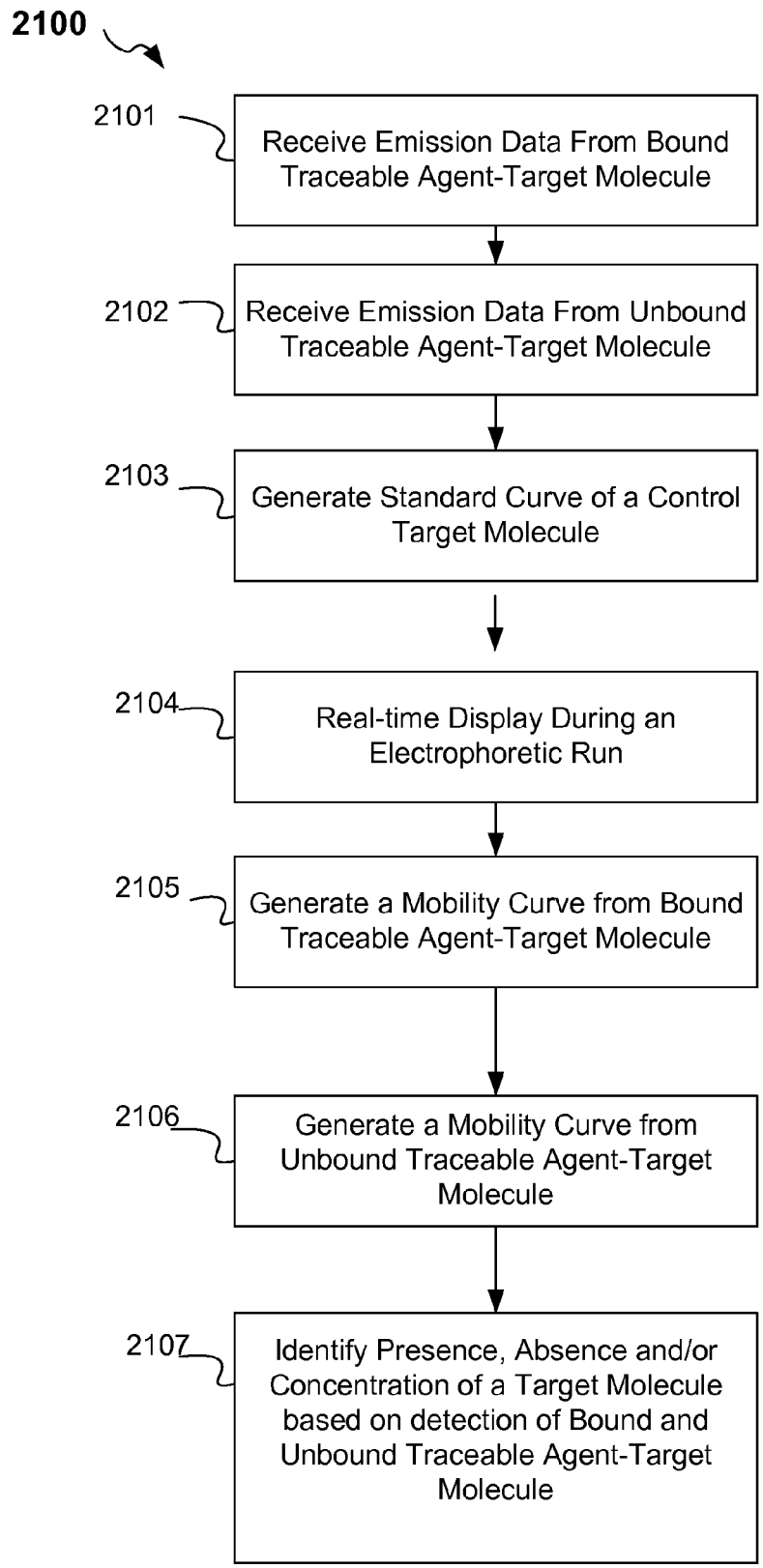

APPARATUS, COMPOSITIONS AND METHODS FOR RAPID COMPETITIVE HOMOGENEOUS ASSAY

RELATED APPLICATIONS

The present application claims the benefit of U.S. Provisional Patent Application Ser. No. 60/993,034, filed Sep. 10, 2007 and Ser. No. 60/995,186, filed Sep. 25, 2007, incorporated herein by reference in their entirety.

FIELD

Embodiments herein generally relate to apparatus, methods, and/or compositions for rapid detection and/or determination of concentration of and/or presence of target molecules in a sample. Certain embodiments relate to detection and determination of concentration and/or presence of target molecules using apparatus and systems disclosed herein. Methods, compositions and/or apparatus are effective for detection and/or concentration measurement over a wide range of concentrations of the target molecule(s).

BACKGROUND

Detection of proteins at low concentrations is of paramount importance in the areas of medicine, food testing, biological research, and the detection of biowarfare agents. One of the most common tools for measuring proteins are antibodies, for example, immunoassays. One common alternative to using whole antibody molecules is to use just the binding regions of the antibody. For example, a variety of antigen-binding antibody fragments are known, such as Fab fragments, Fab' fragments, $F(ab)_2$ fragments, $F(ab')_2$ fragments, or scFv fragments.

Another recently alternative to antibodies for measuring target molecules are aptamers. Aptamers are nucleic acids molecules that can be obtained for use in measuring target molecules. Aptamers offer some advantages of being produced in vitro in a comparatively short time, of having a long shelf-life, being easy to modify chemically, and of potentially exhibiting better binding characteristics than antibodies but production of aptamers is high cost, and often stability is low in some biological fluids.

Present methods for detecting and/or determining the concentration of molecules in solution fail to combine short assay time, high sensitivity and ability to assay larger sample volumes required to detect and/or quantify target molecules present at very low concentration.

SUMMARY

Embodiments herein relate to devices, methods and composition for detection and/or determination of target molecules. In certain embodiments, methods herein concern detection and/or determination of a wide range of concentration of proteins or other target molecules. In accordance with these embodiments, compositions and methods may concern using binding agents such as antibodies, aptamers, biological receptors or designed small-molecule binders for detection and/or determination of a target molecule concentration using methods and devices disclosed herein.

Other embodiments relate to detection of target molecules in a sample by competitively binding an unlabeled target molecule and traceable agent-target molecule complex with a solution phase agent conjugated to a capture agent. In certain embodiments, the solution phase agent can be an antibody, an antibody fragment, biological receptor, an aptamer, or specially selected small-molecule binder that has been conjugated to a capture molecule. In certain embodiments, a capture molecule can be an avidin such as streptavidin, neutravidin, oligonucleotide primers, or peptide nucleic acid (PNA) primers. In accordance with these embodiments, a solution phase agent can bind to a solution-phase polymer conjugated to the conjugate of the capture molecule and reduce electrophoretic mobility of the solution phase agent during gel electrophoresis. Thus, bound traceable agent-target molecule complex are readily separated from unbound traceable agent-target molecule complex during molecular separation techniques such as electrophoresis, providing two populations of target molecules. In addition, these two populations can be measured providing an inversely proportional and a proportional signal to the target molecule concentration. Differences in electrophoretic mobility between the target molecule/solution phase agent/polymer complex and the unbound target molecule permits this process to be both rapid and effective.

In certain embodiments, the specific antibody can bind to a solution-phase polymer conjugated to the capture molecule in order to reduce the antibody's electrophoretic mobility. Thus, bound traceable agent-target protein molecule complexes can be separated from unbound traceable agent-target protein molecule by a separation method, for example, electrophoresis. These two populations can then be measured providing both inversely proportional and proportional signals to the target protein molecule concentration using specific monoclonal or polyclonal antibodies. In accordance with these embodiments, a large difference can be generated in electrophoretic mobility between a target/antibody/polymer complex and an unbound target permitting separation, rapid detection and determination of a target molecule of interest.

In certain embodiments, the disclosed methods convert a sandwich immunoassay from a heterogeneous assay to a homogeneous assay, thereby eliminating many of the labor-intensive and costly steps normally associated with heterogeneous assays such as the sandwich ELISA assay. In other embodiments, the disclosed methods gain the kinetic advantages associated with performing an assay completely in the solution phase. Embodiments herein may allow a sandwich immunoassay to be performed in minutes instead of hours and at a reduced cost.

Other embodiments relate to systems designed to assess, read and/or record data provided by methods disclosed herein. In certain embodiments, devices disclosed herein provide for visual inspection and assessment of presence or absence and/or quantification in realtime of target molecules of interest. Some embodiments contemplated herein permit separation of target molecules in a gel-free system. In accordance with these embodiments, an apparatus contemplated herein can be a reaction chamber. In certain exemplary reaction chambers, assessment of presence or absence and/or concentration of a target molecule may be assessed in less than one hour, or less than 45 minutes, or less than 30 minutes or less than 15 minutes. One exemplary reaction chamber can include, but is not limited to, at least two electrode (e.g. positive and negative platinum electrode) (901), at least two electrode terminals (902) at least two buffer reservoirs (903), at least two rubber gaskets (e.g. silicon) (904), dialysis membranes (905) positioned at the upper and lower ends of a reaction chamber, at least one quartz reaction channel (906), at least two channel brackets (907) and at least two voltage delivery channels (908) positioned between at least two buffer reservoirs and at least one reaction channel. Other embodiments disclosed herein include an apparatus contemplated as part of a system. In accordance with these embodiments, a system can include an apparatus, a voltage source (e.g. a voltage source that provides for about 10 v/cm to about 1,000 v/cm), a laser (e.g. continuous wave laser) (1001), a laser beam (1002), a shaping prism (e.g. a laser line beam shaping prism) (1003), a reaction chamber (900), a reaction channel (906), light emission (e.g. emitted fluorescent light) (1006) or color emission, lenses and filters (1007), a camera (e.g. a charge-coupled device camera) (1008) and optionally, a computer to receive data from the system. In certain embodiments, a system can also include a loading device (e.g. automated) (1101), rotating drum (1102) and multiple reaction chambers (1103) for analysis of multiple assays.

In certain embodiments, membranes (e.g. dialysis membrane) contemplated of use herein can include any dialysis membrane, for example, commercially available dialysis membrane. In accordance with these embodiments, dialysis membranes are positioned at the top and optionally at the bottom of a reaction chamber. In certain embodiments, dialysis membranes are in direct contact with top and bottom reaction chambers.

It is contemplated herein that disclosed reaction chambers be arranged as a single channel assay or a multi-channel assay. A single channel reaction chamber assay can be a stand-alone reaction chamber capable of positioning on a benchtop or a handheld transportable reaction chamber device. A single channel reaction chamber is contemplated to allow placement of a sample from a subject into a gel-free reaction chamber and separation results from the sample can readily be analyzed in a laboratory or outside a laboratory setting.

Other embodiments contemplated herein can include a computer and computer software for receiving, recording, manipulating and/or displaying data obtained by compositions and methods disclosed herein. In certain embodiments, for example, represented in FIG. 12, screen capture of an exemplary software may include an image captured by a camera (1008). Further embodiments of a software program contemplated herein may allow selection of an area to be analyzed, for example for band intensity analysis and/or evaluation of target molecule complex concentrations. In accordance with these embodiments, it is anticipated that a computer software program will allow for evaluation and analysis of multiple reaction chamber experiments and target molecule analysis within a variety of samples. As represented in FIG. 12, right window, parameters for each assay run can be set, for example, exposures time, time between exposures, number of exposures, and then data can be displayed permitting on-line analysis of the data.

In one embodiment, a computer software program may be used to assess the presence or concentration of a target molecule in a sample. In another example, multiple samples may be assessed for the presence or absence of a target molecule. Parameters of a sample, such as origin relating to the subject and sampling from the subject can be used to identify each sample. In addition, parameters related to preparation of a sample and binding agent used for identification of the sample can be analyzed relative to other samples. Optimum conditions can be derived from a software program contemplated herein in order to increase reproducibility and consistency in sample preparation and analysis. In addition, data obtained by sample analysis can be used for assessing presence of a condition, presence of a contaminant, presence of an agent or progression of a condition represented by presence or various concentrations of an agent in a subject from which a sample is derived. Subjects contemplated herein can be a human or an animal. Alternatively, a sample may be derived from a place or surface rather than a subject. Data obtained from analysis of assays disclosed herein may be used to assess a need for administration of a treatment of the subject with at least one therapeutic agent. These assays may be used through-out a therapeutic treatment of the patient in order to continually analyze the progression of the treatment if presence, absence or concentration levels of a target molecule are associated with a condition of the subject. In another embodiment, these tests may be used in conjunction with other tests in order to gain a more thorough understanding of the overall condition of a subject being tested.

BRIEF DESCRIPTION OF THE DRAWINGS

FIG. 10 represents an exemplary schematic of an apparatus (1000) contemplated herein including, but not limited to, (1001) 473 nm continuous wave laser, (1002) Laser beam, (1003) Laser line beam shaping prism, (900) Reaction chamber, (901) Platinum electrode, (906) Quartz reaction channel, (1004) Emitted fluorescent light, (1005) Lenses and filters, and (1006) Charge-coupled device (CCD) camera.

FIG. 21 represents a flow chart of an exemplary method for assessing presence or concentration of a target molecule in a sample having exemplary operations for generating a standard curve in accordance with some embodiments disclosed herein.

DEFINITIONS

Figure 1:
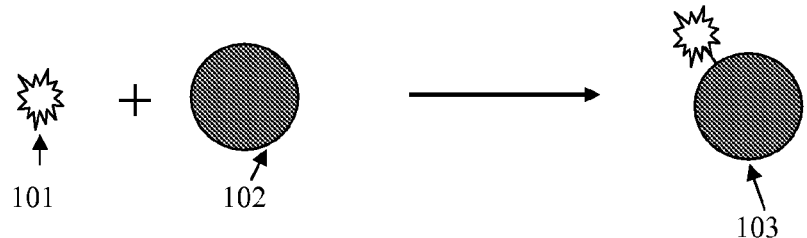
FIG. 1 represents an exemplary schematic of attaching a traceable molecule (101) (e.g Fluorescein) to a target molecule (102) to form a traceable target molecule (103).

As used herein, "a" or "an" may mean one or more than one of an item.

As used herein, vessel can include, but is not limited to, tube, channel or container.

DETAILED DESCRIPTION

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well-known methods or components have not been included in the description.

Embodiments herein relate to devices, methods and composition for detection and/or determination of target molecules. In certain embodiments, methods herein concern detection and/or determination of a wide range of concentrations of proteins or other target molecules in a sample. In accordance with these embodiments, compositions and methods may concern using binding agents such as antibodies, antibody fragments, aptamers, biological receptors, or designed small-molecule binders for detection and/or determination of a target molecule using methods and devices disclosed herein.

Theoretical Treatment of Molecular Movement

As contemplated herein, a particle (which may be a molecule) moving through a fluid experiences a frictional force proportional to its velocity, its size (as described by its hydrodynamic radius), and the viscosity of the fluid. The formal expression of this as shown in Equation 1 (see exemplary equations) is known as the Stokes equation.

The quantity known as the mobility is defined from Equation 1, such that the particle velocity divided by the mobility gives the frictional force. For a spherical molecule, the hydrodynamic radius is equivalent to the radius. For a non-spherical molecule, it can be defined as the radius of a spherical molecule that would behave equivalently under creeping flow conditions (which can be theoretically derived if the shape of the molecule is known). The mobility, as extracted from Equation 1, is expressed in Equation 2a. If a spherical shape is assumed for a molecule of known molecular weight, then the radius is calculated as shown in Equation 2b. Substituting Equation 2b into Equation 2a yields an expression for the mobility in terms of the molecule's density, molecular weight, and viscosity of the fluid, as shown in Equation 2c.

The particle moves at a constant velocity when the frictional force due to this movement is equal to an applied force (e.g. gravity, a voltage gradient). Setting the frictional force equal to the applied force and solving for velocity represents the particle's velocity as the applied force multiplied by the mobility, as shown in Equation 3. The mobility therefore provides a convenient way for calculating particle velocity. The force experienced by a molecule in an electrical field is proportional to the charge on the molecule and the strength of the field. The velocity of the molecule is therefore given by Equation 4, where the quantity designated by "u" is known as the electrophoretic mobility (in units of $cm^2/V$ sec), defined by Equation 5. The factor $10^7$ in Equation 5 converts the charge e into cm-g-s units with volts (which is a m-kg-s unit).

Note that Equation 4 implies that negatively charged molecules (negative ions) move in the opposite direction than positive ions. In the more general form of Equation 4, the velocity of the particle and the electrical field (which is the gradient of the voltage) are vector quantities, and thus have directions associated with them.

The mobility is also closely related to the Svedberg Coefficient s, which is defined as the velocity at which a particle sediments in water at 20° C. in a centrifuge, divided by the centrifugal acceleration. The Svedberg Coefficient is expressed in units of $10^{-13}$ seconds. Using the buoyancy force in Equation 3 to find the velocity, the Svedberg Coefficient as a function of mobility is given by Equation 6a. The mobility can therefore be derived from the Svedberg Coefficient as shown in Equation 6b.

In some embodiments, binding agents can be used that associate or bind specifically to a target molecule of interest. In some more particular embodiments, antibodies, aptamers or other specifically designed molecules may be used that bind to a target molecule of interest. In certain embodiments, one of the most common type of antibodies found in serum can be directed to bind to a target molecule, for example, immunoglobulin G (IgG or gamma-globulin). IgG has a molecular weight of approximately 150 kDa (1320 amino acid residues). The isoelectric point for different IgG molecules ranges from 6 to 7.5, implying a moderate negative charge to a slight positive charge at neutral pH. The Svedberg Coefficient for IgG is around 7. Assuming a density of about 1.2 $g/cm^3$, the mobility as calculated from Equation 2b is $2.1 \times 10^7$ s/g, while the mobility as calculated from Equation 6b is $1.7 \times 10^7$ s/g.

The difference between these two calculations come from at least three sources: (1) IgG is not a perfectly spherical molecule, and thus the mobility as determined by sedimentation should be lower; (2) the density of IgG is not known precisely, and this uncertainty is exaggerated in the second calculation and minimized in the first; and (3) the Svedberg Coefficient used in the second calculation is only approximately known. In certain embodiments, mobility of IgG can be estimated at $2 \times 10^7$ s/g.

Reliably measuring protein concentrations has led to the development of an abundance of assays involving antibodies or antibody-like molecules. A wide variety of immunoassays are known in the art and contemplated herein. Some descriptions below use antibodies as the binding agents, but many other agents are contemplated herein such as aptamers, specifically designed binding agents as well as antibody fragments for example Fab fragments or aptamers. In certain embodiments, choosing a signaling system is important but not necessarily central to methods disclosed herein. Fluorescent tags can be conjugated to binding agents disclosed herein. For example, molecules such as FITC or rhodamine can be conjugated to antibodies to provide a fluorescent signal. In other embodiments, conjugated enzymes can be conjugated to a binding agent, for example alkaline phosphatase or horseradish peroxidase if a colormetric assay is desired, or with enzymes such as carbonic anhydrase or urease if a conductivity assay is desired. In accordance with these embodiments, enzymatic assays typically require addition of a proper enzyme substrate.

Immunoassays

Immunoassays can be characterized as either "heterogeneous" or "homogeneous." Some confusion by those skilled in the art exists as to what these terms mean. In some cases, the term "heterogeneous" can imply that bound complexes are separated (by any means) from the unbound molecules before detection, while the term "homogeneous" implies that little or no separation takes place. Alternatively, the term "heterogeneous" contemplated herein can mean that an assay can use both a solid and a solution phase, in which attachment of a complex to a solid phase allows the unbound molecules to be washed away (or bound molecules to be washed away depending on the phases) before detection of a complex. In addition, as contemplated herein, the term "homogeneous" can mean that the binding, separation (if any), and detection steps occur in a solution phase. In many cases, these differing definitions make little difference in how an assay is classified, as most separation or washing steps involve binding to a solid support, and thus assays involving separation or washing would be classified as heterogeneous by either definition. One exception is separation by electrophoresis, where an assay would likely be classified as heterogeneous according to the first set of definitions, and homogeneous according to the second set of definitions. It is contemplated that embodiments disclosed can rely principally on the second set of definitions.

Therefore, as disclosed in certain embodiments herein, a heterogeneous assay includes binding an antibody-target molecule complex to a surface during a test procedure and then washing away unbound target molecule, other agents within a sample and unbound antibody prior to determining the presence and/or measuring amount of target molecule in the sample. A homogeneous assay, on the other hand, permits a sample and antibodies to be mixed together and determining the presence and/or measuring amount of target molecule in the sample determined without binding to a surface or washing.

Heterogeneous assays can have high sensitivity and specificity and can be performed in formats that provide for very high-throughput testing systems. These formats can also be adapted to test for most target molecules. One limitation includes slow testing times requiring relatively sophisticated instrumentation to perform in large numbers, and the added costs associated with the surface-binding and washing steps.

Homogeneous assays can be very fast, are easily adaptable to new proteins, peptides or other molecules and platforms, and can be very cost effective. Limitations may include potentially lower specificity and sensitivity. In addition, these formats may be restricted to small target antigens. Therefore, both homogenous and heterogeneous assays are contemplated herein depending on need, samples being analyzed and target molecules of interest.

One embodiment of a quantitative competitive immunoassay can include an antibody bound to a solid support and both labeled and unlabeled target in solution that are allowed to bind to the antibody. A labeled target can compete for a limited number of antigen binding sites with the unlabeled target. A label on a target molecule can be a radioisotope, an enzyme or a fluorescent molecule. A signal generated using this type of immunoassay is inversely proportional to the concentration of unlabeled target.

Many homogeneous competitive immunoassays exist in the art. Generally, homogeneous immunoassays are advantageous since separation of bound and free ligands is often not necessary thus simplifying instrumentation. Here, all binding occurs in a solution phase therefore these methods tend to be rapid.

General advantages of these techniques include: (1) simplification of assay development due to the requirement for only a single binding agent, for example an antibody, (2) a typically faster assay time than traditional two-site assays, (3) quantitative measurement across a broad analytical range, and (4) the ability to work with targets that are too small to permit the binding of two antibodies simultaneously (e.g. sandwich assays).

Homogeneous immunoassays provide one or more signals that are inversely proportional to the target concentration. This fact makes it very difficult to measure small concentrations with this technique since small changes in a small signal can be more reliably measured than small changes in a large signal. Specificity is only being derived from a single binding event and sensitivity of a homogenous assay can be improved using a high quality antibody.

A few descriptions of some common technologies follow. This list is not exhaustive and is not meant to exclude any other homogeneous competitive assays that may be known in the art.

Some of the earliest homogeneous competitive assays involve monitoring the formation of insoluble antigen-antibody complexes, for example, using polyclonal antibodies. Briefly, since target specific polyclonal antibodies can recognize multiple epitopes on a target and are bivalent, large complexes of target and antibody can form when the target and antibody concentrations are roughly equal. These complexes can grow in size to the point that they become insoluble. These insoluble complexes retard or scatter light passed through the sample matrix. The scattered light can be measured by nephelometry, or conversely, the attenuation of the light through the sample can be measured by turbidimetry. The signal generated is proportional to the quantity of target present in the sample. This technique works well for analytes that are present at relatively high levels and are of sufficient size to have multiple antigen binding sites. Note that as target concentration increasingly exceeds antibody binding sites, the ability of multiple antibodies to concurrently bind the same antigen is decreased. Therefore, by including a known concentration of purified antigen in the assay mixture, such that antibody-antigen complex formation is maximized, the assay can be made competitive; the addition of antigen with the sample to be assayed can result in a decrease in complex formation. Some limitations can include a need for multiple binding sites and unsuitability for low concentration measurements. This method can also be affected by sample matrix variations and a lack of specificity.

An additional homogeneous competitive immunoassay is the Fluorescence Polarization Immunoassay (FPIA). A FPIA is dependent on the rate of rotation of a molecule or complex in solution. Larger molecules or complexes rotate more slowly than smaller molecules or complexes. When polarized light of appropriate wavelength is passed through the sample, polarization of fluorescently emitted light is maintained if the molecule or complex is rotating slowly enough. If the unbound, fluorescently-labeled target is small enough so that its rate of rotation is sufficiently rapid, then the emitted light is depolarized. If the fluorescently-labeled target binds to the specific IgG, the mass of the complex is increased, slowing the rate of rotation and maintaining the polarization of the emitted light.

In certain systems, the FPIA assay system includes a target-specific antibody, a fluorescently labeled target and the unlabeled target that is to be quantitated. Labeled and unlabeled targets compete for a limited number of binding sites on a specific IgG. Polarized fluorescent signal is inversely proportional to the concentration of the unlabeled target. This method is attractive for its simplicity and speed. The FPIA is limited to small molecule targets and sacrifices analytical range for sensitivity.

There are a number of other competitive homogenous assays, for example, CEDIA™, EMIT™, the prosthetic-group immunoassay, the enzyme-channeling immunoassay and the substrate-labeled fluorescence immunoassay. These methods are competitive and generally involve activation or inactivation of an enzyme or enzyme complex upon binding of an antibody to a target. These methods have similar benefits and limitations to FPIA.

Affinity Probe Capillary Electrophoresis (APCE)

Capillary electrophoresis involves applying a voltage, by means of positively and negatively charged electrodes, across a long capillary filled with an ionic buffer, thereby causing charged molecules to migrate toward one electrode or the other (Oda and Landers, 1997). One common complication is known as "electro-osmotic flow". Glass capillaries tend to have negatively charged surfaces, which are associated with positively charged ions in solution near the surface. These positively-charged ions migrate toward the negative electrode (the cathode), dragging the bulk solution with them. This electro-osmotic flow causes all ions to migrate toward the cathode (although at different rates) and is usually put to good use, as a single detector can analyze all ionic species regardless of charge as they flow past. Electro-osmotic flow can be eliminated or even reversed by changing the electrical characteristics of the capillary wall.

For APCE, a target molecule is incubated with a cognate antibody, which has been conjugated to a detection molecule, usually a fluorescent probe. The mixture is then injected into the capillary, and a voltage is applied, setting up electro-osmotic flow. The free target, the free antibody, and the target/antibody complex will migrate at different rates, and can therefore be detected as separate peaks by a fluorescent detector (the free target should not yield a signal).

Electrophoresis

Electrophoresis is a technique that may be used in place of the washing of complexes bound to a solid support, thereby converting what is normally a heterogeneous protein assay into a homogeneous assay. Electrophoresis is commonly used to separate molecules (e.g. large molecules such as proteins or nucleic acids) based on their size and electrical charge. Positive and negative electrodes are placed in a solution containing the molecules to be separated, and a voltage drop is applied between the electrodes. In general, positively charged molecules will migrate toward the negatively charged electrode, while negatively charged molecules will migrate toward the positively charged electrode. Generally, the speed at which the molecules migrate is directly proportional to their charge, and inversely proportional to their size. For example, small, highly charged molecules move faster than large, lesser charged molecules. However, densely packed molecules move faster than loosely conformed molecules, so that two molecules of the same mass and charge may migrate at different rates. Higher voltage drops cause faster migration, while higher concentrations of other charged molecules in the solution cause slower migration.

There are many variations of electrophoresis known in the art. A solution through which the molecules move may be free, usually in capillary tubes, or it may be embedded in a matrix. Common matrices include polyacrylamide gels, agarose gels, and filter paper. The matrix serves to sieve the molecules according to size, leading to better separations. The pH (acidity) of the solution affects the charge of the molecules, and may be varied (even from one end of the matrix to the other) to affect the migration rate of the molecules. A solution may include denaturing agents such as urea, which cause protein and nucleic acid molecules to unfold, so that migration rates for molecules of the same mass and charge will be identical. A sample to be electrophoresed may be prepared with a detergent such as SDS, which coats all proteins to nullify charge differences, so that migration rates depend on mass, but not on charge. However, for most assays requiring binding agents, for example, antibodies, antibody fragments or aptamers, both the protein and the binding agents may need to be kept close to their natural state, so that processes that change the pH or denature the proteins are typically not viable options.

Detection of a Protein

Certain embodiments herein concern converting heterogeneous competitive assays to homogeneous competitive assays. In one embodiment, a heterogeneous competitive immunoassay can be converted to a homogeneous competitive immunoassay. In some embodiments, certain advantages for these conversions include reducing some labor-intensive and costly steps and limitations normally associated with a heterogeneous competitive immunoassay. In addition, these conversions allow for several formats of the homogeneous immunoassay. In other embodiments, other potential kinetic advantages can be associated with performing an assay contemplated herein nearly or completely in the solution phase. In yet other embodiments, compositions, methods and apparatus for a homogeneous competitive assay for larger molecules are contemplated. For example, these assays can be an immunoassay or assay using other binding agents. In certain embodiments, a competitive immunoassay can be performed in minutes instead of hours at reduced costs and with enhanced sensitivity for target molecules.

In exemplary embodiments, agents of use may include one or more of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, Pseudomonas endotoxin, an antisense oligonucleotide, an interference RNA, or a combination thereof.

Aptamers

In certain embodiments, a binding agent of use may be an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20 C) and R' is alkyl (1-20 C); in addition, this group may be attached to adjacent nucleotides through O or S. Not all linkages in an oligomer need to be identical.

The aptamers used as starting materials in the process of the invention to determine specific binding sequences may be single-stranded or double-stranded DNA or RNA. In a preferred embodiment, the sequences are single-stranded DNA, which is less susceptible to nuclease degradation than RNA. In preferred embodiments, the starting aptamer will contain a randomized sequence portion, generally including from about 10 to 400 nucleotides, more preferably 20 to 100 nucleotides. The randomized sequence is flanked by primer sequences that permit the amplification of aptamers found to bind to the target. For synthesis of the randomized regions, mixtures of nucleotides at the positions where randomization is desired may be added during synthesis.

Methods for preparation and screening of aptamers that bind to particular target molecules of interest are well known in the art and are contemplated herein. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) are retained during separation. Each cycle results in an enrichment of aptamers with high affinity for the target. Repetition for between three to six selection and amplification cycles may be used to generate aptamers that bind with high affinity and specificity to the target molecule of interest.

Imaging Agents and Radioisotopes

In certain embodiments, target molecules, for example, peptides or proteins may be attached to imaging agents of use for imaging and diagnosis of various diseased organs, tissues or cell types. Many appropriate imaging agents are known in the art, as are methods for their attachment to proteins or peptides. Certain attachment methods can involve the use of a metal chelate complex employing, for example, an organic chelating agent such a DTPA attached to the protein or peptide. Target molecules also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium $^{36}$chlorine, $^{57}$cobalt, $^{58}$cobalt, copper$^{62}$, copper$^{64}$, copper$^{67}$, $^{152}$Eu, fluorine$^{18}$, gallium$^{67}$, gallium$^{68}$, $^3$hydrogen, iodine$^{123}$, iodine$^{124}$, iodine$^{125}$, iodine$^{131}$, indium$^{111}$, $^{52}$iron, $^{59}$iron, $^{32}$phosphorus, $^{33}$phosphorus, rhenium$^{186}$, rhenium$^{188}$, Sc$^{47}$, $^{75}$selenium, silver$^{111}$, $^{35}$sulphur, technicium$^{94m}$ technicium$^{99m}$ yttrium$^{86}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art. These fluorescent labels are preferred for in vitro uses, but may also be of utility in vivo applications, particularly endoscopic or intravascular detection procedures.

In alternative embodiments, target molecules may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. These and other luminescent labels may be obtained from commercial sources such as Molecular Probes (Eugene, Oreg.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin. Diagnostic immunoconjugates may be used, for example, in intraoperative, endoscopic, or intravascular tumor or disease diagnosis.

In various embodiments, labels of use may comprise metal nanoparticles. Methods of preparing nanoparticles are known. Nanoparticles may also be obtained from commercial sources (e.g., Nanoprobes Inc., Yaphank, N.Y.). Modified nanoparticles are available commercially, such as Nanogold® nanoparticles from Nanoprobes, Inc. (Yaphank, N.Y.). Functionalized nanoparticles of use for conjugation to proteins or peptides may be commercially obtained.

Cross-Linkers

In some embodiments, proteins or peptides may be labeled using various cross-linking reagents known in the art, such as homo-bifunctional, hetero-bifunctional and/or photoactivatable cross-linking reagents. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithio-bispropionimidate; N-succinimidyl-3-(2-pyridyldithio)propionate; 4-(bromoaminoethyl)-2-nitrophenylazide; and 4-azidoglyoxal. In an exemplary embodiment, a carbodiimide cross-linker, such as DCCD or EDC, may be used to cross-link acidic residues to amino or other groups. Such reagents may be modified to attach various types of labels, such as fluorescent labels.

Bifunctional cross-linking reagents have been extensively used for a variety of purposes. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described (U.S. Pat. No. 5,889,155, incorporated herein by reference). The cross-linking reagents combine a nucleophilic hydrazide residue with an electrophilic maleimide residue, allowing coupling in one example, of aldehydes to free thiols. The cross-linking reagent can be modified to cross-link various functional groups.

As known in the art any distinguishable component may be covalently linked or attached in any manner to a target molecule of interest for detection in a sample.

Symbols:
a=centrifugal acceleration [cm/s2]
e=unit charge of electrons or protons [1.6×10-19 C (coulombs)]
f=applied force [g cm/s2]
ff=frictional force [g cm/s2]
r=hydrodynamic radius of the molecule [cm]
m=mobility [s/g]
M=molecular weight [g/mole]
N=Avogadro's Number (6.023×1023/mole)
s=Svedberg Coefficient [10-13 s]
u=electrophoretic mobility [cm2/s-V]
v=velocity of the particle through the fluid [cm/s]
z=net charge on the molecule
η=viscosity of fluid [g/cm-s]
ρ=density of the molecule [g/cm3]
ρf=density of the fluid [g/cm3]
ψ=electrical field [volt/cm]

$$f_f = 6\pi r \eta v \qquad \text{(Equation 1)}$$

$$m = v/f_f = 1/(6\pi r \eta) \qquad \text{(Equation 2a)}$$

$$r = \sqrt[3]{\frac{3V}{4\pi}} = \sqrt[3]{\frac{3M}{4\pi N \rho}} \qquad \text{(Equation 2b)}$$

-continued $$m = \sqrt[3]{\frac{N\rho}{162\pi^2 \eta^3 M}} \qquad \text{(Equation 2c)}$$

$$v = fm \qquad \text{(Equation 3)}$$

$$v = zem\psi = u\psi \qquad \text{(Equation 4)}$$

$$u = ezm \times 10^7 \qquad \text{(Equation 5)}$$

$$s = v/a \cdot 10^{13} = \frac{(\rho - \rho_f)}{\rho_f} \frac{M}{N} amla \cdot 10^{13} \qquad \text{(Equation 6a)}$$

$$m = \frac{\rho N s}{(\rho - \rho_f) M} \times 10^{13} \qquad \text{(Equation 6b)}$$

$$m = \sqrt[3]{\frac{(6 \times 10^{23})(1.2)}{162\pi^2 (0.01)^3 (1.5 \times 10^5)}} = 2.1 \times 10^7 s/g \qquad \text{(Equation 7a)}$$

$$m = \frac{(1.2)(6 \times 10^{23})(7 \times 10^{-13})}{(1.2 - 1.0)(1.5 \times 10^5)} = 1.7 \times 10^7 s/g \qquad \text{(Equation 7b)}$$

Computer Software

In certain embodiments contemplated herein, software applications of use for methods disclosed herein pertaining to reaction chamber and systems having one or more reaction chambers (e.g. EVEIA assay and the EVEIA instrument) can be written using any software known in the art for such methods. A software development program, for example Java Developers Kit (e.g. JDK 1.5.06) and an Eclipse integrated development environment (e.g. version: 3.2), including some adapter software to interface with drivers supplied with purchased hardware can be used. Software used herein is highly modular, consisting of over one hundred classes (software modules) written, which in turn are dependent on the hundreds of classes included in the JDK. The Eclipse IDE combines an advanced code editor with a compiler and a file management system.

Users of the software view a suite of at least three different applications. In one application, software controls an apparatus, collects and saves data to a file, and provides real-time display during a run. In another application, software provides a redisplay of data generated during a run. Additionally, a third application allows the comparison of data from different runs. All applications allow simple data analysis (peak height and area).

In other embodiments, a controller application consists of two or more windows. At least one window displays an image captured by a camera, and provides a means for the user to select a region of interest for image analysis. At least a second window provides control of an assay's data acquisition, including exposure time, time between exposures, and total length of the run. At this time, control of an instrument is limited to turning on a laser at specified times and for specified lengths of time (or controlling a shutter to effect the same result), requesting the camera to capture an image for a specified exposure time, and requesting that the image be downloaded to the computer. Baseline data can also be acquired or loaded from previously saved runs. A file saved for each run contains the raw data for each individual time point, saved in sequence. Changing how the data is displayed (as detailed in the next paragraph) does not change the data that is saved.

In certain embodiments, the second window for the controller application (see FIGS. 13A-13B) can also display data on a real-time basis, and provide means for changing how the data is displayed. The data may be displayed as the raw image of the region of interest for each exposure (for example see FIG. 12, left panel), as a plot of image intensity averaged radially across the region of interest versus axial position, or both. Height of each plot, y-scale, and amount of y-overlap (from none, to full overlap) between neighboring plots, may all be changed on a real-time basis through the graphical user interface. In addition, regions on the plots may be selected by a user for simple data analysis (peak height and area), which is displayed on a real-time basis. This data-display feature is common to all the applications in the suite, and is an example of the modular basis of the software, as the same class is used in all cases.

In other embodiments, a second application allows for replay (see for example, FIG. 13B) of any run saved in the controller application. In appearance, it is largely identical to the second window of the control application; however buttons and fields having to do with control of a run are replaced with buttons and fields necessary to retrieve a saved run, and control how it is displayed. For instance, a saved run may be re-displayed as a movie by limiting the number of plots displayed to one, and by having a sequence of plots (representing individual time points) displayed at 200 millisecond intervals.

Figure 14:
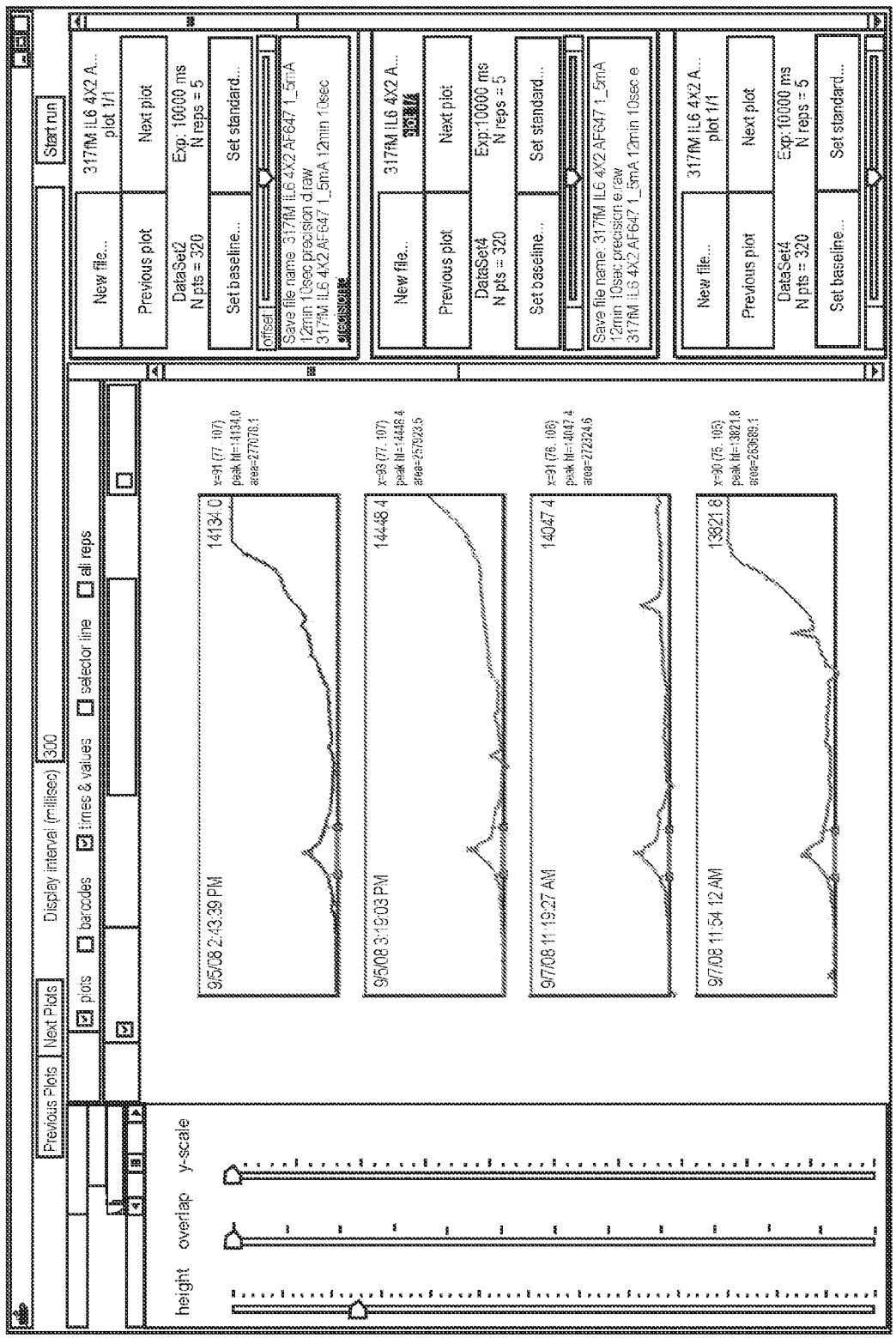
FIG. 14 represents an exemplary screen capture of software used for some embodiments contemplated herein.
Figure 15:
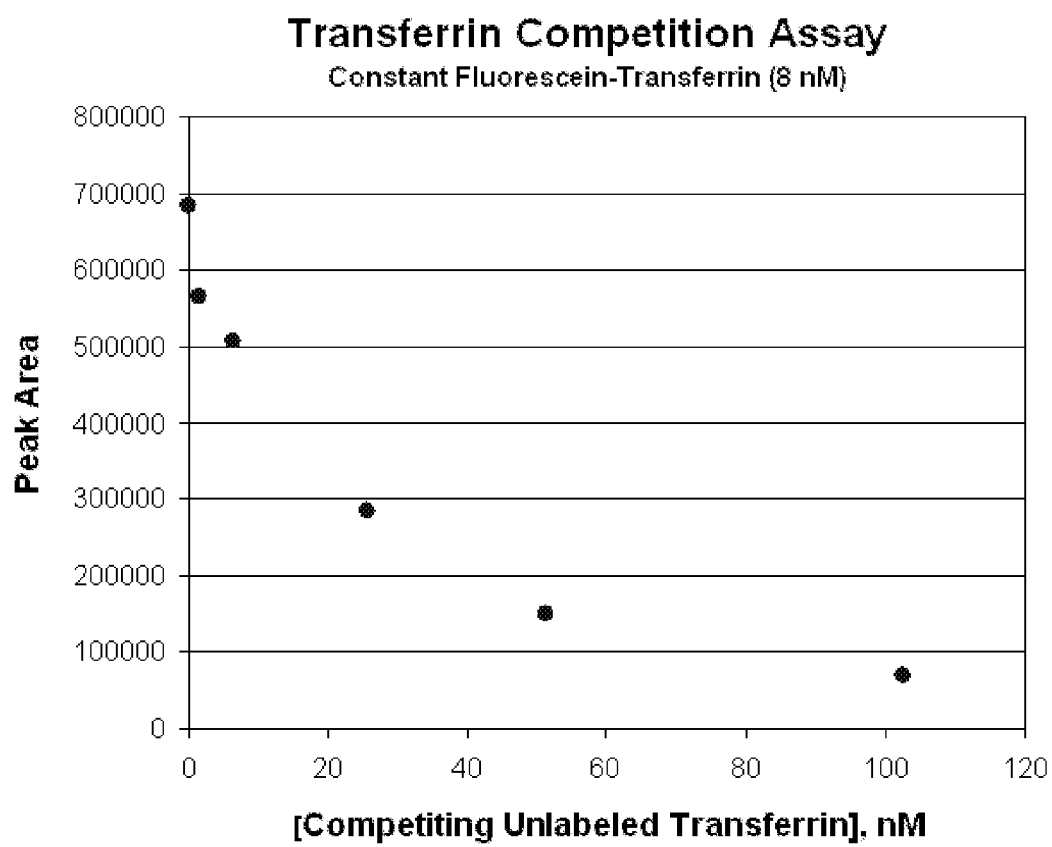
FIG. 15 represents exemplary data from peak areas of the plots from FIG. 13, as well as other unlabeled transferrin concentrations between 0 and 102 nM, calculated at 10 minutes for the various concentrations, and the resulting plot is illustrated.
Figure 16:
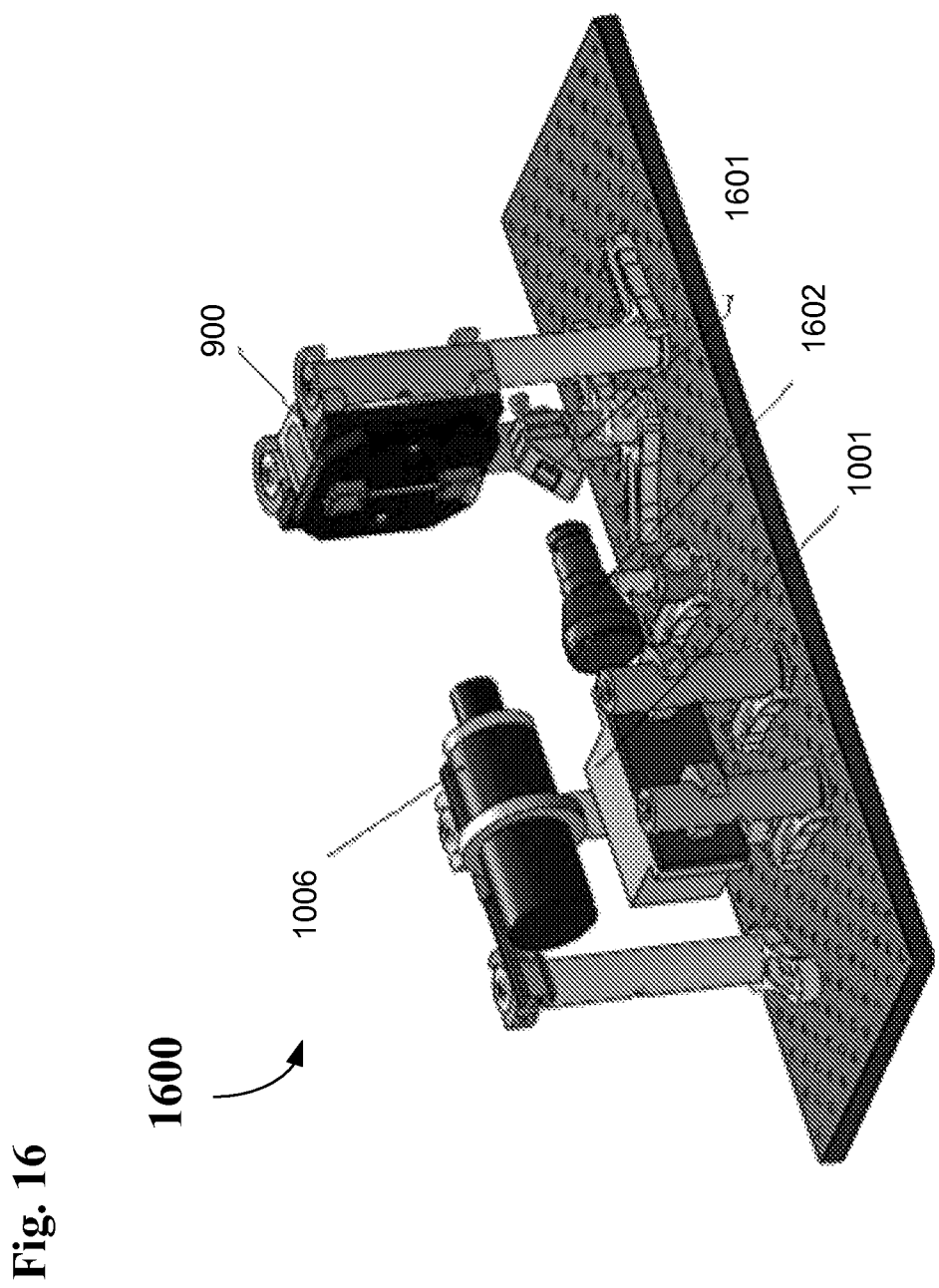
FIG. 16 represents a view of an exemplary system disclosed herein. This exemplary diagram represents a side-on view of a reaction chamber (900), a camera (1006), a laser (1001), a beam director (e.g. a 45 degree beam director) operably connected to the laser (1601), and a beam expander (e.g. a Galilean Beam Expander AR Coating: 350-650 nm) (1602). In one exemplary embodiment, a system represented in FIG. 16 may be the size of a bread box such as 5-6 inches by 16 inches or even 5 times or 10 times smaller, in order, for example, to allow portability.
Figure 17:
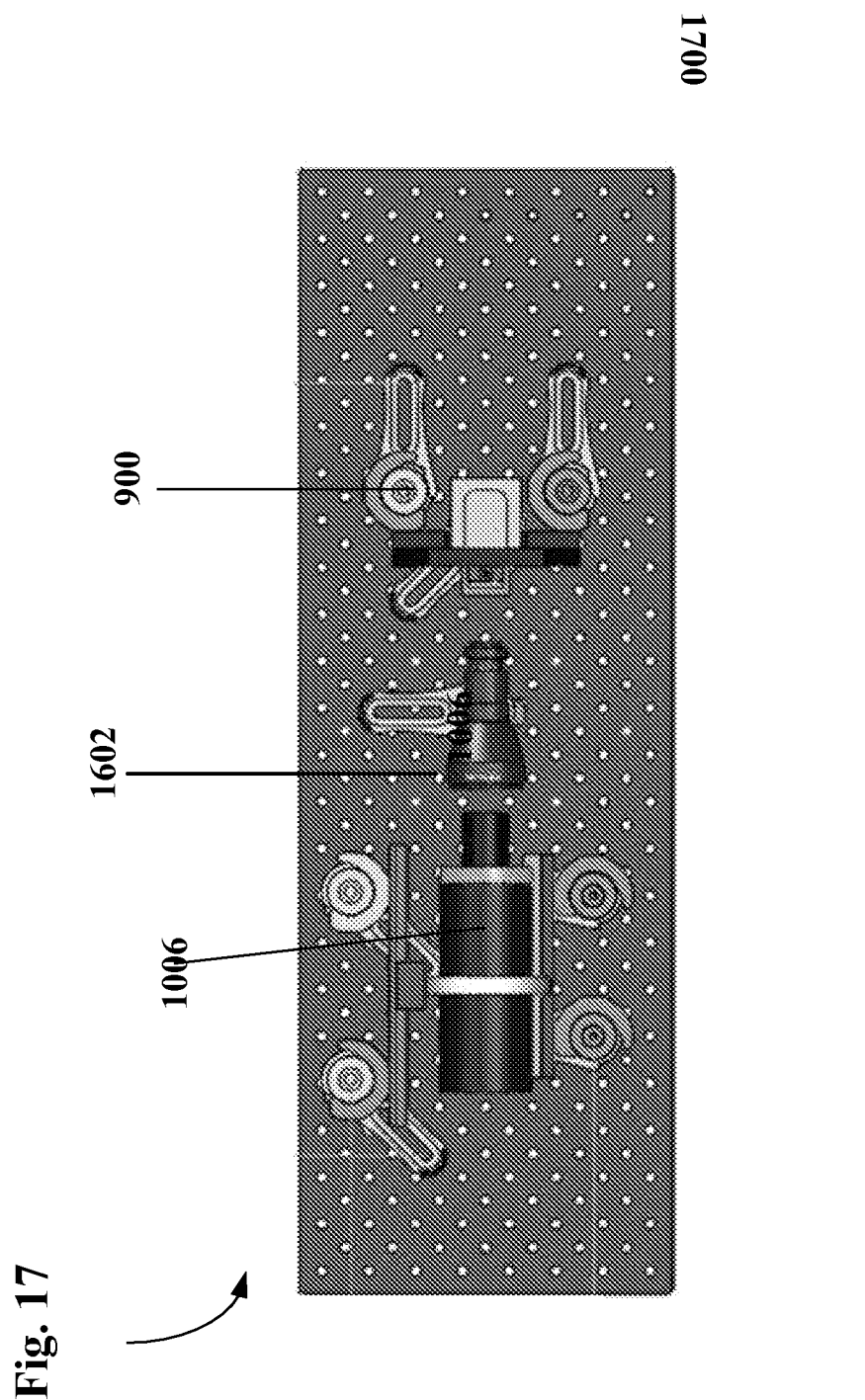
FIG. 17 represents a view of an exemplary system disclosed herein. This exemplary diagram represents a top view of a reaction chamber (900), a camera (1006) and a beam expander (e.g. a Galilean Beam Expander AR Coating: 350-650 nm) (1602).
Figure 18:
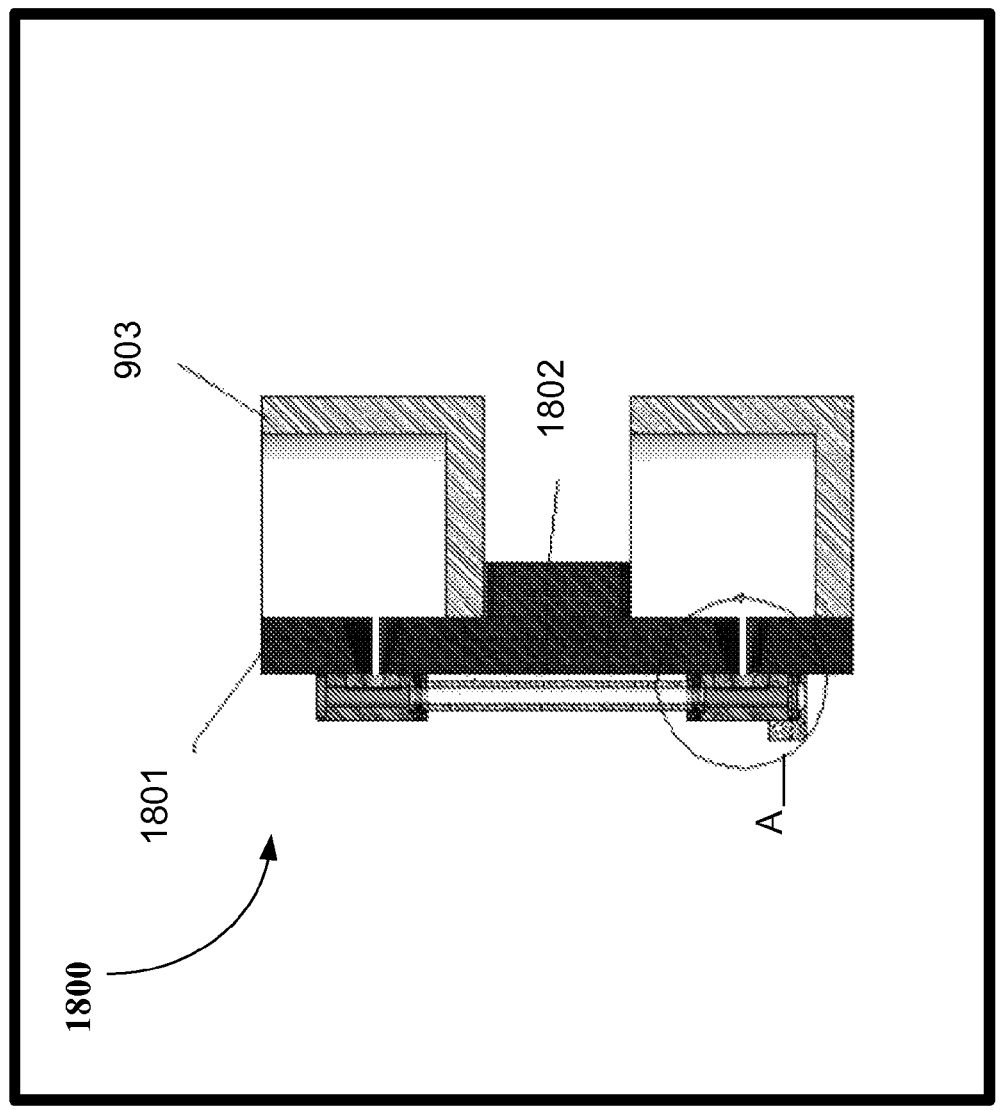
FIG. 18 represents a view of an exemplary apparatus disclosed herein. This exemplary diagram represents a top view of a reaction chamber (900) with a chamber mount plate (e.g. a Delrin Chamber Mount Plate) (1801), a reservoir (a Delrin Buffer Reservoir) (903) and a backer plate (e.g. Delrin Backer Plate) (1802), and A indicates a diagrammatic circle that is represented in an enlarged view in FIG. 19.
Figure 19:
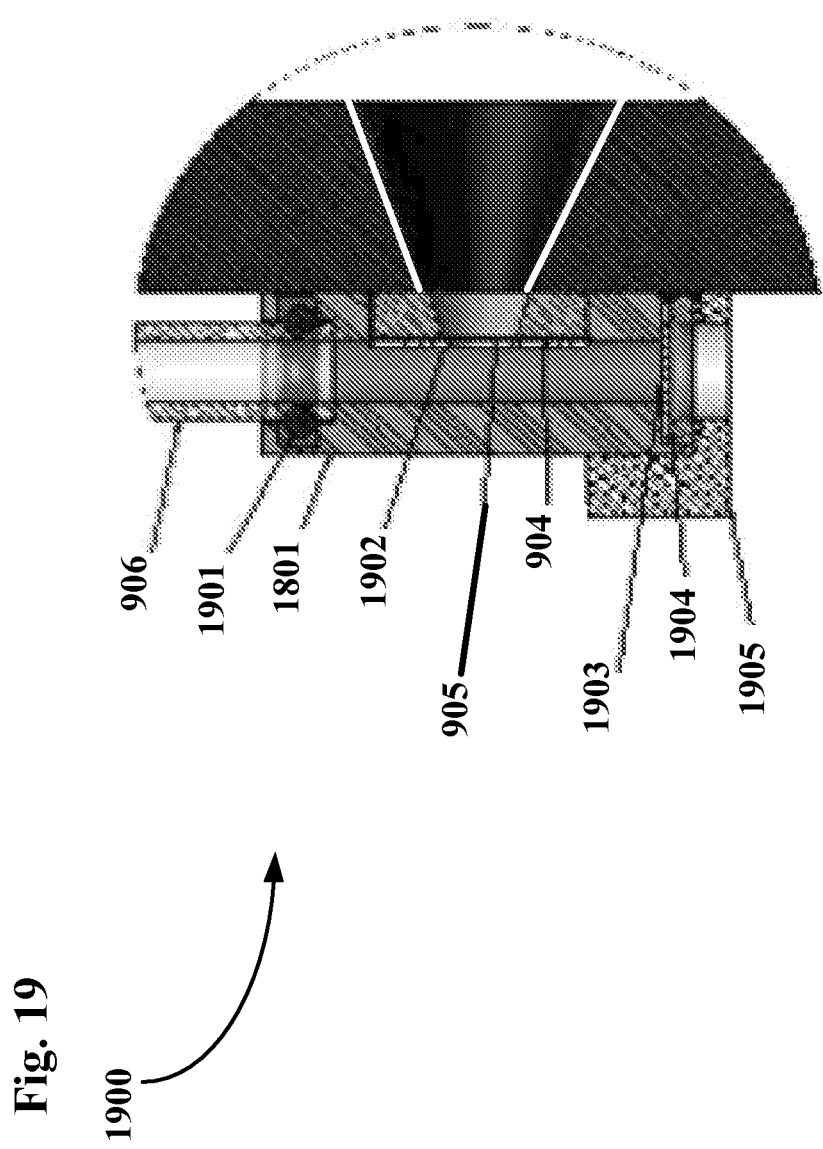
FIG. 19 represents a view of an exemplary apparatus disclosed herein, also represented in reduced size in FIG. 18 as A. This exemplary diagram represents a side view of a reaction chamber (900) having a quartz reaction chamber (906), a chamber seal (e.g. silicon reaction chamber seal) (1901), a mount (e.g. a Delrin Reaction Chamber Mount) (1801), a window (e.g. a sizing window) (1902), a membrane (e.g. dialysis membrane) (905), a gasket (e.g. a silicon reaction chamber gasket) (904), a different window from 1902 (e.g. a sapphire window) (1903), a window seal (e.g. a silicon sapphire window seal) (1904) and a window holder (e.g. a Safire window holder) (1905).

In yet other embodiments, a third application allows for a display and comparison of plots from data saved for different runs (see for example, FIG. 14). Currently, saved files from around ten different runs may be selected for display. Any single plot (representing a single time point) from each run may be displayed along with single plots from all other selected runs. Time points may be displayed in sequence either forward or backward for individual runs, or for all runs in lock step.

Systems

Other embodiments disclosed herein relate to systems designed to run assays, gather data from the assays and analyze the assay information contemplated herein. Other embodiments concern systems that assess, read, record and/or manipulate data provided by methods disclosed herein. In accordance with these embodiments, an apparatus that can be part of a system disclosed herein can be a reaction chamber. One exemplary reaction chamber can include, but is not limited to, at least two electrodes (e.g. platinum electrodes, anode and cathode) (901) each operably-connected to at least one electrode terminal (902) In addition, each electrode is positioned in at least one buffer reservoir (903) at each end of the reaction chamber (e.g. top and bottom) wherein each buffer reservoir has at least one rubber gasket (e.g. silicon) (904). In accordance with these components that may make up a reaction chamber, a reaction chamber can further comprise one or more dialysis membrane(s) (905) (e.g. on the top and bottom of the reaction chamber) at least one quartz reaction channel (906), at least one channel bracket (907) and at least two voltage delivery channels (908) positioned between at least one buffer reservoir and at least one reaction channel.

Other embodiments disclosed herein include an apparatus including a reaction chamber that is part of a system. Systems contemplated herein can include, but are not limited to, a voltage source, a laser (e.g. continuous wave laser) (1001) positioned to interact with a reaction chamber (900); a laser beam (1002) emitted from the laser, a shaping prism (e.g. a laser line beam shaping prism) (1003) capable of directing beam emission from a deflected laser beam from a traceable agent-target molecule complex within in a reaction chamber (900), a reaction channel (906), light emission (e.g. emitted fluorescent light) (1006), lenses and filters (1007) operably connected to a camera (e.g. a charge-coupled device camera) (1008) and optionally, a computer to receive data from the system. In certain embodiments, a system can also include a loading device (e.g. automated) (1101) for loading a sample onto a reaction chamber; a rotating drum (1102) capable of rotating from one reaction chamber to the next and multiple reaction chambers (1103) positioned around the rotating drum. One feature of this system is the ability to measure the presence or absence of a target molecule using a traceable agent and a detection system wherein detection or measuring the concentration of a target molecule can be assessed in one hour or less, 45 minutes or less, 30 minutes or less, or 15 minutes or less.

Figure 12:
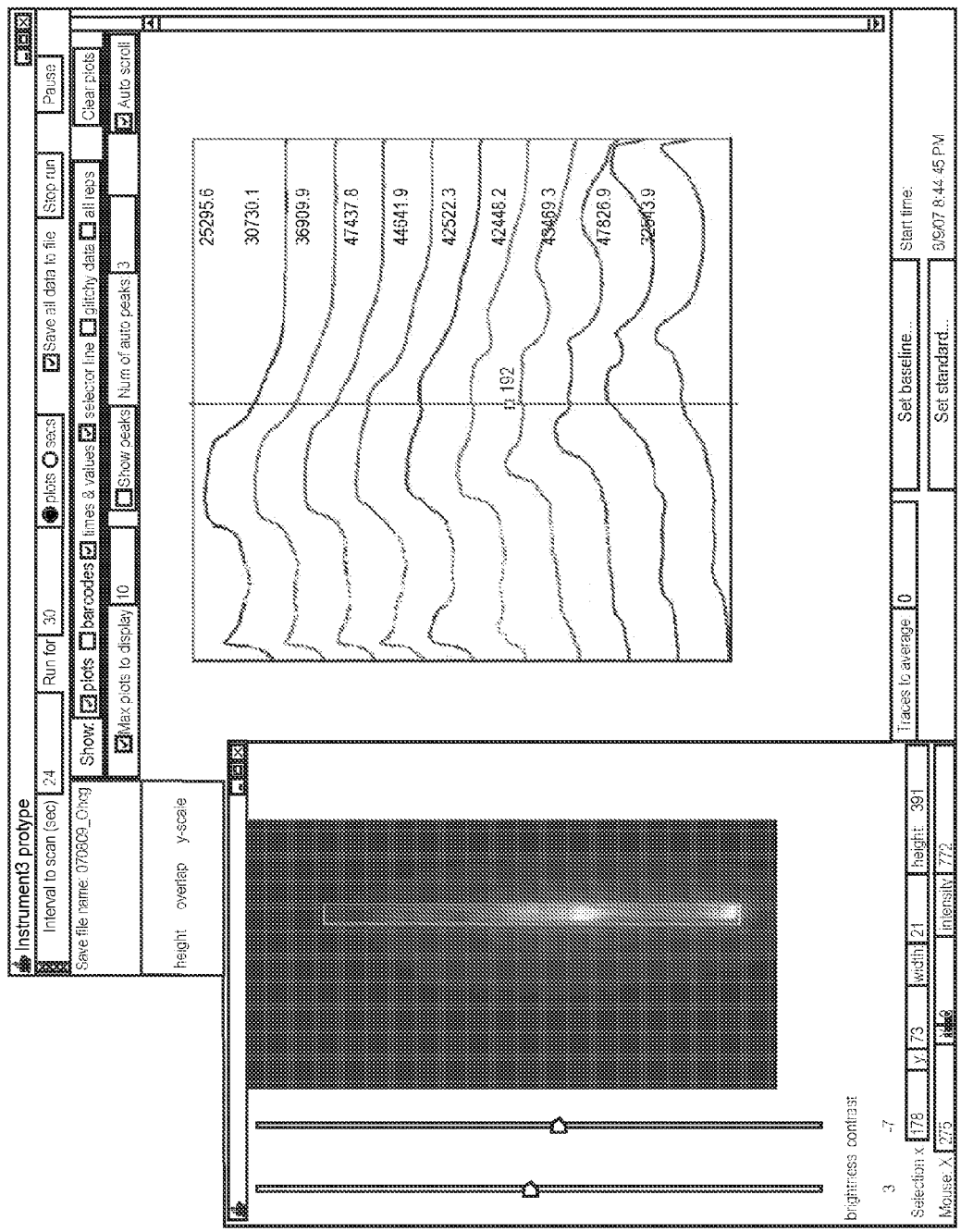
FIG. 12 represents an exemplary screen capture of software of some embodiments contemplated herein. The left window represents an image captured by a CCD camera (1102), and allows selection of the area to be analyzed. The right window sets parameters for assays contemplated herein (for example exposures time, time between exposures, number of exposures), displays the data representative of one or more assays, and allows on-line analysis of the data.
Figures 13A, 13B:
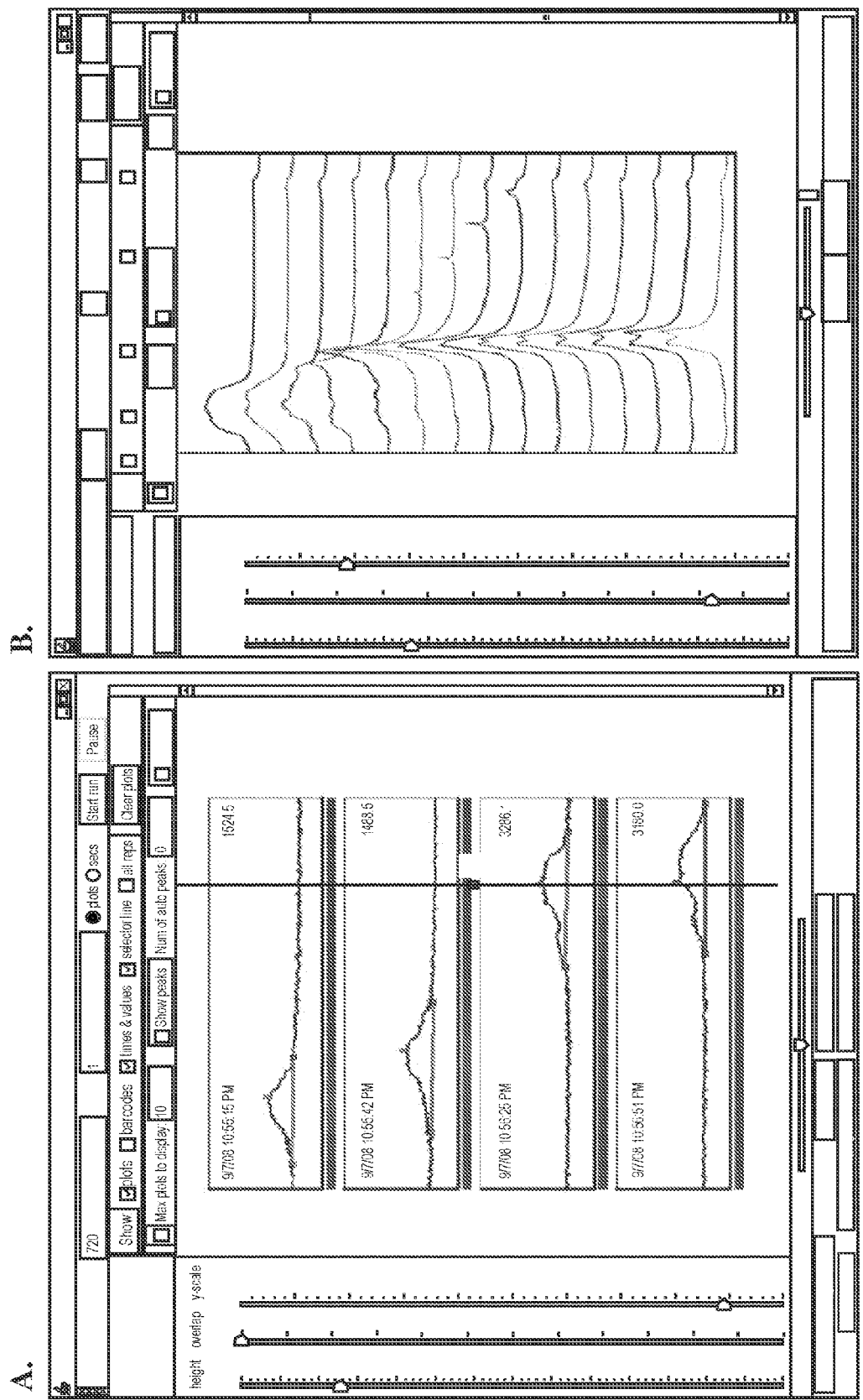
FIGS. 13A-13B represent exemplary screen captures of software used for some embodiments contemplated herein.

Other embodiments contemplated herein can include a computer and computer software for recording, manipulating and displaying data obtained by compositions and methods disclosed herein. In certain embodiments, for example, represented in FIG. 12, screen capture of an exemplary software may include an image captured by a camera (1008) Further embodiments of a software program contemplated herein may allow selection of an area to be analyzed, for example for band intensity analysis and/or evaluation of target molecule complex concentrations. In accordance with these embodiments, it is anticipated that a computer software program will allow for evaluation and analysis of multiple reaction chamber experiments and target molecule analysis within a variety of samples. As represented in FIG. 12, right window parameters for each assay run can be set, for example, exposures time, time between exposures, number of exposures, and then data can be displayed permitting on-line analysis of the data.

Axial Delivery of Light

Some embodiments disclosed herein concern a system or apparatus where excitation light can include axial delivery to a reaction chamber, and detection occurs through walls of the reaction chamber. One advantage of this technique over light delivery through the walls of a column or vessel is that full intensity of an original light source can be delivered throughout the entire length of the column. In certain embodiments, if light is delivered through walls of the column, light may require spreading to effectively cover the length of the column, thereby diminishing its intensity. In other embodiments, light to be delivered (e.g. laser light or other comparable light) may need to be collimated for an even intensity distribution throughout the column. The light may be aimed axially through a column directly from a source, or a light source may be directed by mirrors or prisms. Optionally, if the light is delivered through the bottom of the column, an optically clear window (e.g. sapphire, quartz, glass, or optically clear plastic) or equivalent may require positioning at the bottom of the column to allow entry of the light. In other embodiments, if the light is delivered through the top of a column, additional steps may be needed to deal with the lensing effect of a meniscus formed by the fluid components at the top of the column.

Exemplary Computer System Overview

Figure 20:
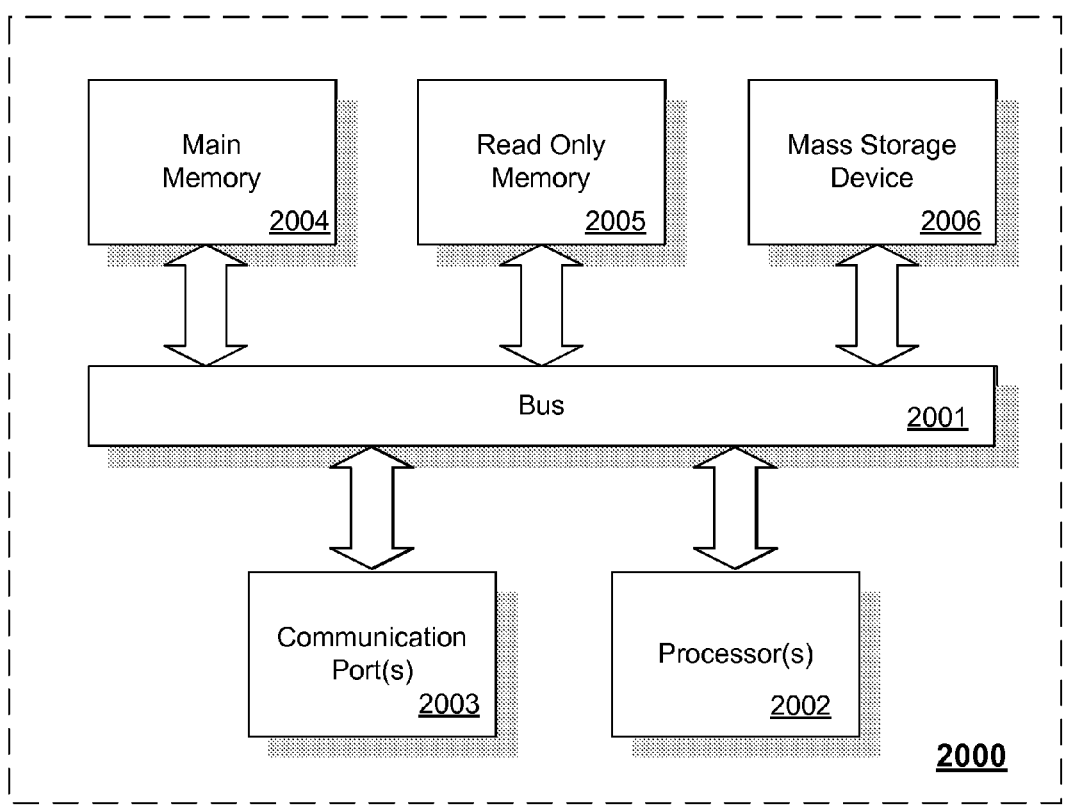
FIG. 20 represents an exemplary computing device.

Embodiments of the present invention include various elements, a variety of which may be performed by hardware components or may be embodied in machine-executable instructions, which may be used to cause a general-purpose or special-purpose processor programmed with the instructions to perform the elements (see for example FIG. 21). Alternatively, the steps may be performed by a combination of hardware, software, and/or firmware. As such, FIG. 20 is an example of a computer system 2000 with which embodiments may be utilized. According to one exemplary method, a computer system includes a bus 2001, at least one processor 2002, at least one communication port 2003, and a main memory 2004. System 2000 may also include a removable storage media (not shown), a read only memory 2005, and/or a mass storage component/device 2007.

Processor(s) 2002 can be any known processor, including, but not limited to, an Intel® Itanium® or Itanium 2® processor(s), or AMD®, Opteron® or Athlon MP® processor(s), or Motorola® lines of processors. Communication port(s) 2003 can be any of an RS-232 port for use with a modem based dialup connection, a 10/100 Ethernet port, or a Gigabit port using copper or fiber. Communication port(s) 2003 may be chosen depending on a network such a Local Area Network (LAN), Wide Area Network (WAN), or any network to which the computer system 2000 connects.

Main memory 2004 can be Random Access Memory (RAM), or any other dynamic storage device(s) commonly known in the art. Read only memory 2005 can be any static storage device(s) such as Programmable Read Only Memory (PROM) chips for storing static information such as instructions for processor 2002.

Mass storage 2006 can be used to store information and instructions. For example, hard disks such as the Adaptec® family of SCSI drives, an optical disc, an array of disks such as RAID, such as the Adaptec family of RAID drives, or any other mass storage devices may be used.

Bus 2001 communicatively couples processor(s) 2002 with the other memory, storage and communication blocks. Bus 2001 can be a PCI/PCI-X or SCSI based system bus depending on the storage devices used.

Removable storage media can be any kind of external hard-drives, floppy drives, 10MEGA® Zip Drives, Compact Disc-Read Only Memory (CD-ROM), Compact Disc-Re-Writable (CD-RW), Digital Video Disk-Read Only Memory (DVD-ROM). Display (not shown) may be any device operable to present visual representations of parametric models (e.g. realtime run displays of assays) and permit users to view, change, and interact with parametric models according to embodiments herein, including but not limited to, graphical web interfaces and computer monitors.

The components described above are meant to exemplify some types of possibilities. In no way should the aforementioned examples limit the scope of the invention, as they are only exemplary embodiments.

In other embodiments, after samples (e.g. potentially having a target molecule of interest) are prepared and loaded onto an exemplary reaction chamber, a receiving operation 2101 receives emission data from either bound traceable agent-target molecule complexes or unbound traceable agent-target molecule complexes. Another receiving operation 2103 receives data and can compute a standard curve for control concentrations of a target molecule of interest. In some embodiments 2100, each of receiving operations may use one or more of the equations disclosed in order to calculate concentrations of a target molecule in a sample. Each system can be configured to analyze one or more target molecules of interest based on operator input. It is contemplated herein that certain disclosed methods and or apparatus may simply measure bound traceable agent-target molecule complexes and not the unbound traceable agent-target molecule complexes.

A generating operation 2103 or 2105 generates a standard curve or mobility curve based on the received data. Another generating operation 2107 generates a concentration curve for a target molecule of interest if present. Those skilled in the art will readily recognize how standard curves can be generated in the generating operations 2103 and 2105.

A deriving operation 2107 derives the amount of target molecule present in a sample. Generally, the deriving operation 2107 generate model data based on selected data points or a selected emission value by the operator representative of a sample.

Immunoassays

The importance of measuring protein concentrations in a reliable fashion has led to the development of an abundance of assays involving antibodies or antibody-like molecules. The wide variety of immunoassays currently in use have been described in depth by Gosling (1990), incorporated by reference herein. The descriptions below use antibodies as the binding agents, but in many cases Fab fragments or aptamers could be used instead. However, the methods and compositions described herein are not so limited and in other alternative embodiments, binding agents may be, e.g., biological receptors. A number of such receptors (e.g., insulin receptor, insulin-like growth factor 1 receptor, acetylcholine receptor, GABA receptor, antiotensin receptor, glucagon receptor, chemokine receptors, cytokine receptors, etc.) are well known in the art and any such known receptor or their ligand-binding fragments may be used in the practice of the claimed methods.

Detection and or determination of concentration is typically provided by labeling an antibody or other binding molecule with a signal moiety, such as a fluorescent, chemiluminescent, radioactive or other tag known in the art, allowing the binding molecule to bind to the target, and detecting or measuring the amount of light emission, radioactivity, etc. associated with bound antibody. In most cases, the choice of signaling system is not central to the method. Molecules that are conjugated to antibodies such as FITC or rhodamine for a fluorescent signal can usually be replaced with enzymes such as alkaline phosphatase or horse radish peroxidase if a colorimetric assay is desired, or with enzymes such as carbonic anhydrase or urease for conductivity assays. However, enzymatic assays require the addition of the proper substrate.

A commonly used alternative to conjugating the signaling molecule directly to the antibody that binds the target protein (primary antibody), is to employ a secondary antibody conjugated to the signaling molecule. A secondary antibody is an antibody developed to bind to all antibodies from a certain species (and must therefore be from a different species). For instance, antibodies may be harvested from a goat that has been injected with rabbit antibodies. If these secondary antibodies are conjugated to a signaling molecule, then the binding of the secondary antibody to the primary antibody provides attachment of the signaling molecule to the primary without chemical conjugation. This secondary antibody can be used to attach a signaling molecule to any primary antibody derived from the same species, thereby adding a degree of modularity to the assay.

Heterogeneous immunoassays are often described without specifying the type of solid support to which binding occurs. However, the types of solid supports used represent significant variations in any immunoassay process, affecting both the procedure and the time needed for different steps, and sometimes the type of detection that will be used. For instance, in its most common form, the sandwich ELISA involves binding complexes to the bottom surface of wells in a microtiter plate, which allows for easy manual introduction of reagents for washing, and easy reading of fluorescent or colormetric signals. However, the assay may take several hours due to mass-transfer limitations. It takes time for proteins to equilibrate between the bulk solution and the stagnant layer at the surface, and multiple washes are usually called for. These problems may be mitigated to some extent by using microbeads as the binding surface, which puts the surface into more intimate contact with the bulk solution, as well as drastically increases the surface area available for binding per unit volume of solution. The solid phase (on the beads) is then separated from the solution phase during washing either by filtration or centrifugation. This process may be made more amenable to automation by using paramagnetic beads, which are easily separated from the solution phase magnetically. Nearly all of the heterogeneous immunoassays could be modified to use these different surfaces.

There are two common types of immunoassays in use for detection and/or determination of molecule concentration in samples that are somewhat analogous to the methods described herein. The first, sandwich ELISA, is considered the gold standard for immunoassays in terms of specificity. This high degree of specificity is achieved by requiring the simultaneous binding of two separate antibodies to the target of interest, a technique that is also used in the methods described below. The second is the Affinity Probe Capillary Electrophoresis assay (APCE). This assay consists of binding the target of interest to a single primary antibody, then running the mixture through a capillary electrophoresis device to separate bound antibody from unbound antibody. The electrophoretic separation allows the entire assay to be performed in solution, a technique that is also used in the methods described below.

Kits

Contemplated herein are kits for performing methods herein. A kit can include, but is not limited to, one or more reaction chamber compositions and containers for generating a reaction chambers for carrying out disclosed methods. Alternatively, a kit may include only reagents, aside from the sample, for performing the disclosed assays.

Sandwich ELISA

The sandwich Enzyme-Linked ImmunoSorbant Assay (ELISA), was previously developed and has been considered the gold standard for protein detection, exhibiting very high specificity and precision as its primary advantages. Some disadvantages are the time involved to detect a protein and the large number of steps required. Often Elisas take between two and six hours to perform, depending on the stringency and number of washes, and time-length of incubation steps.

A first step in an Elisa is to bind a primary antibody to the target protein to the bottom surface of the wells, that surface having been prepared to promote protein binding. The surface is then treated with a blocker such as bovine serum albumin (BSA), to bind up any remaining active sites, thereby keeping any other proteins from binding and affecting the specificity of the test. The wells are washed multiple times to remove free antibody and blocker.

A sample, presumably containing the target protein, is added to the well and incubated for a predetermined time. Ideally, only this target protein will bind to the surface antibody, and no other protein will bind either to the blocked surface or to the surface antibody. Multiple washes are performed to remove any non-specifically bound proteins. If any non-specific proteins do bind, the next step minimizes their effect.

A second antibody to the target protein, conjugated to a detector molecule, is added to the wells and allowed to bind. Because of this antibody's specificity, very little of it will bind to any protein that is non-specifically bound either to the surface or to the first antibody. Multiple washes are performed to remove any of the unbound second antibody. Because this second antibody is conjugated to a detection molecule, the concentration of this second antibody can be determined and related to the concentration of the target protein in the original sample.

Affinity Probe Capillary Electrophoresis (APCE)

Capillary electrophoresis involves applying a voltage, by means of positively and negatively charged electrodes, across a long capillary filled with an ionic buffer, thereby causing charged molecules to migrate toward one electrode or the other. One common complication is known as "electro-osmotic flow". Glass capillaries tend to have negatively-charged surfaces, which are associated with positively-charged ions in solution near the surface. These positively-charged ions migrate toward the negative electrode (the cathode), dragging the bulk solution with them. This electro-osmotic flow causes all ions to migrate toward the cathode (although at different rates) and as a single detector can analyze all ionic species regardless of charge as they flow past. Electro-osmotic flow can be eliminated or even reversed by changing the electrical characteristics of the capillary wall.

For APCE, the target molecule is incubated with a cognate antibody which has been conjugated to a detection molecule, usually a fluorescent probe. The mixture is then injected into the capillary, and a voltage is applied, setting up electro-osmotic flow. The free target, the free antibody, and the target/antibody complex will migrate at different rates (augmented by the electro-osmotic flow), and can therefore be detected as separate peaks by a fluorescent detector (the free target should not yield a signal). Although capillary electrophoresis is more rapid than ELISA assays, the small volumes of samples that may be analyzed (due to the small size of the capillary) limits the sensitivity of this method to detect proteins or other target molecules present at very low concentration in the sample.

Enhanced Velocity Electro Immunoassay (EVEIA) for Target Molecule Detection and Quantitation Embodiments herein provide for a rapid, highly sensitive method for detecting and determining presence or absence and/or concentration of target molecules in samples involving vertical stacked electrophoresis. Because electrophoretic parts of the EVEIA technique take place in containers of much larger volume and cross-sectional area than microcapillaries, these embodiments have allowed methods of detection of target molecules that are present in low concentration in a sample. Here, electrophoresis may occur in a tube, channel or other container with a minimum hydrodynamic radius (twice the cross-sectional area divided by the circumference) of 0.5 mm or higher. In some embodiment, an exemplary tube interior volume is 2 $mm^3$ or more per length of the tube. In other embodiments, a minimum hydrodynamic radius can be twice the cross-sectional area divided by the circumference of 0.5 mm or higher. For example, a hydrodynamic radius of about 0.75 mm provides a 2 mm3/mm of length. For circular tubes, hydrodynamic radius can be the same as the radius. This embodiment could be used for illustrating flow through irregularly shaped channels.

In other embodiments disclosed herein, essentially uncharged polymer agents may include one or more of linear polyacrylamide, partially-crosslinked polyacrylamide (e.g crosslinked below the point of formation of a solid gel, where compositions remain fluid or liquid) dextran or polyethylene glycol or other similar agents or a combination of agents. In other embodiments, an essentially uncharged polymer agent migrates very little under conditions disclosed herein, for example these agents may migrate about 0.1 to about 1.0 mm/sec under 100 v/cm of applied power. In certain embodiments, a gradient of increasing density may be from 1.0 to 1.1 g/ml within a tube, channel or container. In other embodiments, the gradient can include, but is not limited to, a sample layer of density 1.0 to 1.02 g/ml, a capture layer of density from 1.002 to 1.05 g/ml and a stacking layer from 1.01 to 1.1 g/ml. In all embodiments contemplated herein, a stacking layer will have a higher density than a capture layer, and a capture layer will have a higher density than a sample layer. Optionally, viscosity may be increased as well from top to bottom, to produce a stacking effect at the interface. In certain embodiments, viscosity may be 1 centipoise but will not exceed 1.3. In other embodiments, 2 centipoise can be a maximum upper limit for viscosity of a bottom layer. In certain aspects herein, a mass to charge ratio will increase upon formation of disclosed complexes causing a decrease in electrophoretic mobility of a target molecule. Because the complex contains a very high mass to charge ratio, it becomes essentially immobile at the stacking layer, while unbound components migrate through the stacking layer and are separated from the complex. This can provide a very rapid and sensitive assay that can detect very low concentrations of target molecules in short time.

In some embodiments, methods disclosed herein can consist of the following:

1. Acquiring a first binding agent to a target molecule of interest and conjugating a traceable or trackable agent to some of the target molecules (and not to a percent of other target molecules) in a manner that does not interfere with the specific binding to the target molecule of interest. In certain embodiments, the first binding agent can be a monoclonal antibody, an antibody fragment (e.g., Fab), an aptamer, or any other molecule or complex of molecules that exhibit specific binding to the target of interest. The target of interest may be a protein, a peptide, a protein complex, or any molecule soluble in aqueous solution. The traceable or trackable agent may be a fluorescent molecule, a radiolabel, an enzyme that produces a colorimetric product, a metal ion, an enzyme that produces an electrically detectable product, or any molecule or complex of molecules that can be readily detected and quantified, either directly or indirectly.
2. Acquiring a second binding agent to the target molecule of interest and conjugating a capture agent to it in a manner that does not interfere with the specific binding to the target of interest. This second binding agent could be a monoclonal antibody, a polyclonal antibody, an antibody fragment (e.g., Fab), an aptamer, or any other molecule or complex of molecules that exhibit specific binding to the target of interest. The capture agent could be biotin, streptavidin, a single-stranded nucleic acid, or any other molecule or complex of molecules that can be bound with high specificity and affinity. In certain embodiments, the second binding agent is a polyclonal antibody, and the capture agent is biotin complexed with neutravidin.
3. Acquiring a sample putatively containing some amount of said target of interest, of which amount it is desired to be determined.
4. Preparing a vertical electrophoresis chamber consisting of stacked layers of conductive aqueous solutions, some of which contain uncharged polymers, these layers arranged with increasing densities or viscosities from top to bottom to suppress mixing. The topmost layer will consist of the sample to be measured ("sample layer"). For example the top layer can have a density of 1 g/ml and the layers can increase in each subsequent layer by about 0.2 to 5 percent in density and progress to a density or viscosity of about 0.5 percent, or 2 percent, or 10 percent increase in density or viscosity compared to the density or viscosity of the sample layer. At least one of the layers below the sample layer will contain polymers conjugated to a cognate binding agent of the capture agent ("capture layer"). Optionally, at least one of the layers below a capture layer will contain a relatively high concentration of uncharged polymers, which will serve to impede the mobility of complexes bound to polymers ("stacking layer"). The concentration of uncharged polymers can range from about 0.5% to 20%, weight/volume.
5. Mixing and incubating said first binding agent, said second binding agent, and said target of interest together to allow the formation of ternary complexes, which consist of the first binding agent conjugated to the signaling agent that is bound to the target of interest which is bound to the second binding agent conjugated to the capture agent.
6. Applying an electrical potential from a power source (e.g. a power source capable of producing 10-1,000 v/cm) across the vertical dimension of the electrophoresis chamber containing the mixture. Thus, the target molecules migrate into the capture layer, where complexes will bind to polymers conjugated to a cognate of the capture agent, drastically reducing the mobility of these complexes.
7. Continuing the application of the electric potential thereby effecting a separation between low-mobility complexes bound to polymers, and all other molecules, thus localizing in time and space the signaling agents associated with the target of interest from all other signaling agents.
8. Optionally, continuing the application of the electric potential, thereby causing all target molecules to migrate into the stacking layer, in which the mobility of the complexes is further reduced, leading to a compression of the band containing these complexes, and effecting a further separation between the low-mobility complexes that are bound to polymers, and all other molecules.
9. Measuring the signaling agent in one or more of these said groups of compounds, thereby determining the amount of said target of interest in said sample.

EXAMPLES

The following examples are included to demonstrate certain embodiments presented herein. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

Example 1

In certain embodiments, compositions and methods herein concern measuring the concentration of target molecules in a sample proposed to contain the target molecules. For example, the following may include all or some of the following steps:

Obtaining a target molecule of interest and conjugating a traceable molecule to the target molecule in a manner that does not interfere with specific binding by a binding agent described below. Target molecules contemplated herein may be a protein, a peptide, a protein complex, or any other molecule soluble in aqueous solution. Traceable molecules contemplated herein may be a fluorescent molecule, a radiolabel, an enzyme that produces a signal, for example, a colormetric or luminescent product, an enzyme that produces a electrically detectable product, or any molecule or complex of molecules that can be easily detected and quantified, either directly or indirectly. One exemplary method is illustrated in exemplary FIG. 1, the target molecule is transferrin, and the traceable molecule is fluorescein.

Figure 2:
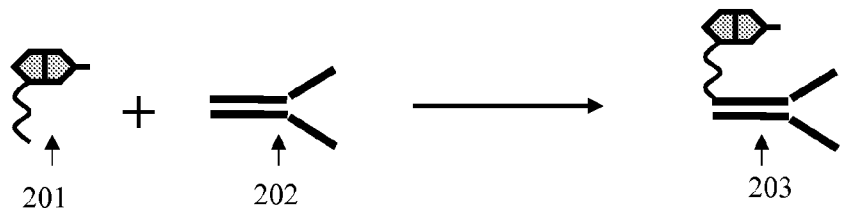
FIG. 2 represents an exemplary schematic of a capture element (104) (e.g. biotin) linked to a binding agent (202) (e.g. an antibody) to form a complex of a capture element-binding agent (203).

Obtaining a binding agent capable of binding the target molecule, and conjugating a capture agent to the target molecule in a manner that does not interfere with specific binding to the target molecule. In certain embodiments, a binding agent may be an antibody, an antibody fragment (Fab), an aptamer, or any other molecule or complex of molecules capable of specifically binding the target molecule. In various embodiments, a capture agent can be a biotin, an oligonucleotide primer, or any molecule that exhibits stable, high-affinity binding to a cognate molecule. One exemplary method can be illustrated in FIG. 2, the binding agent is an antibody, and the capture agent is a biotin-neutravidin complex.

Obtaining a sample putatively containing a target molecule(s) and determining the presence and/or concentration of the target molecule(s). In one exemplary method, a vertical electrophoresis chamber is prepared. In accordance with this method, a chamber can consist of stacked layers of conductive aqueous solutions. Some of these layers contain uncharged polymers. In certain embodiments, these layers can be arranged with increasing densities or viscosities from top to bottom to reduce mixing of the layers. In this example, the topmost layer can consist of a sample to be measured ("sample layer"). At least one of the layers below the sample layer can contain polymers conjugated to a cognate binding agent of a capture agent ("capture layer"). Optionally, at least one of the layers below the capture layer will contain a relatively high concentration of uncharged polymers. In certain embodiments, uncharged polymers can be added to one or more layers allowing the uncharged polymers to bind to a target molecule or a target molecule complex of interest, the association to the uncharged polymers can serve to impede the mobility of complexes bound to polymers ("stacking layer").

Figure 3:
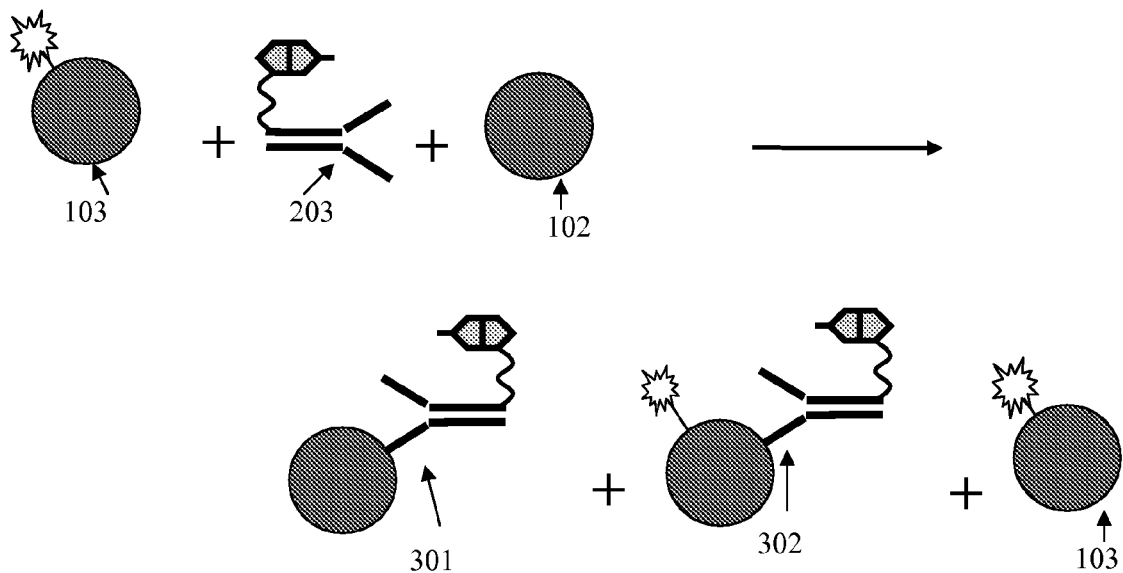
FIG. 3 represents an exemplary schematic of a traceable target molecule (103), a capture element-binding agent (203) and a free target molecule (102) are combined to form complexes (301, 302) and excess traceable agent-target molecule complex (103).
Figure 4:
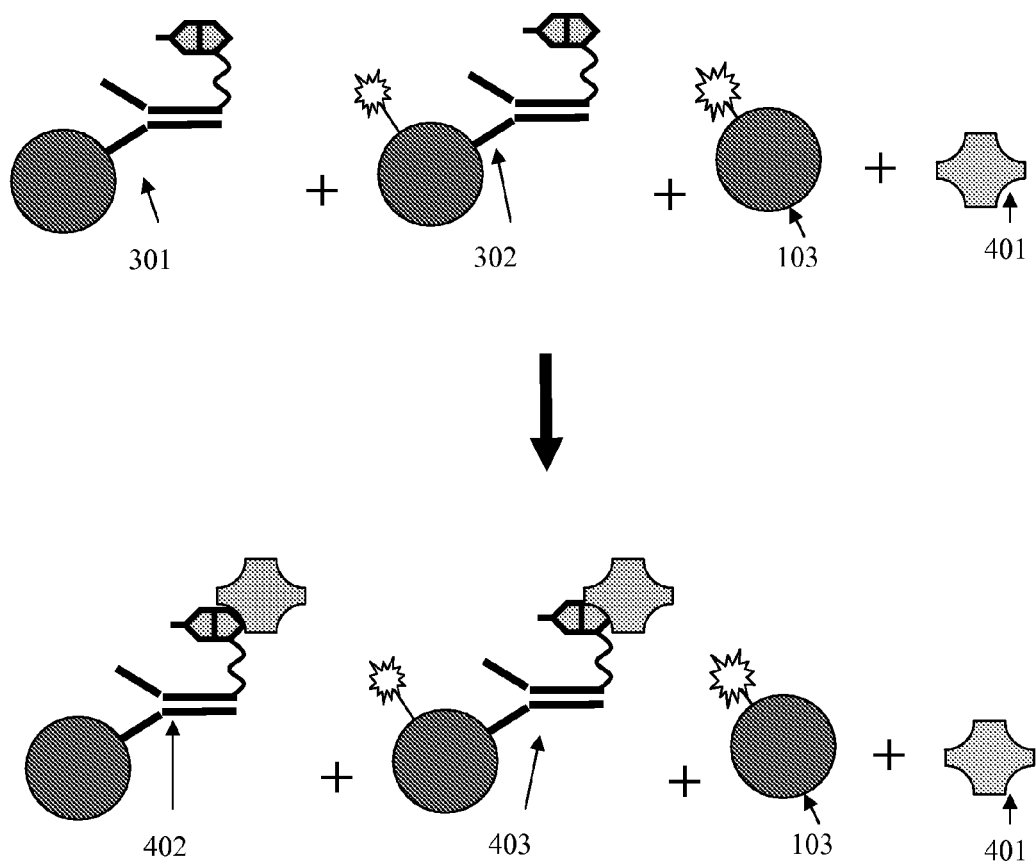
FIG. 4 represents an exemplary schematic of a traceable products from the reaction illustrated in FIG. 3 mixed with an excess of neutravidin (401) to produce complexes of either traceable agent (403) or free target molecule (402) with capture element-binding agent, and a multivalent agent (e.g. neutravidin) (401), as well as excess traceable agent-target molecule complex (103) and neutravidin.
Figure 5:
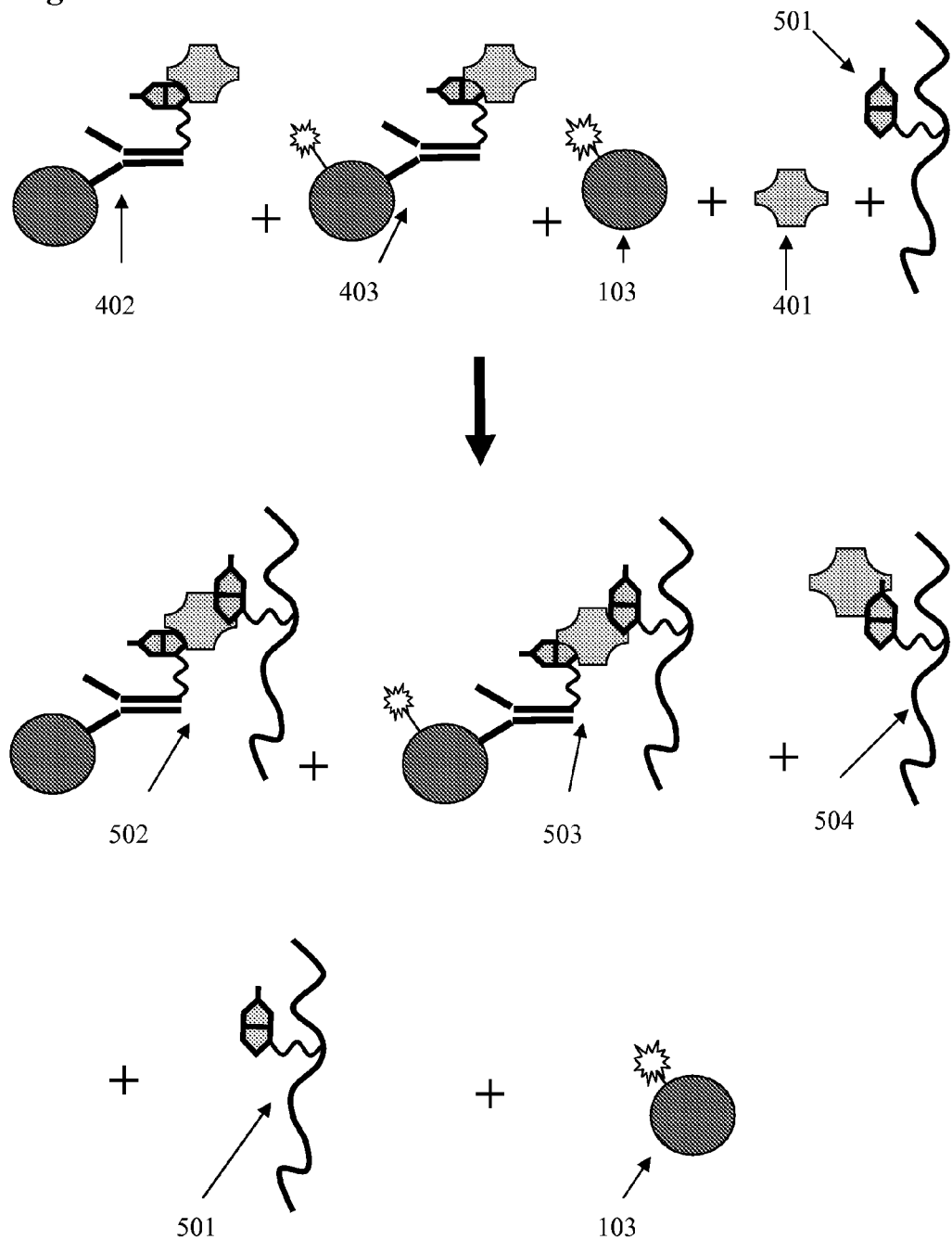
FIG. 5 represents an exemplary schematic of products from a reaction illustrated in FIG. 4 mixed with an excess of multivalent agent (e.g. neutravidin) and an excess of essentially uncharged capturable polymer (e.g. biotin-conjugated polymer) to produce complexes of either the target molecule (502) or traceable agent-target molecule complex (503) with capture element-binding agent and multivalent agent and the capturable polymer, as well as excess capturable polymer (501) and excess traceable agent-target molecule complex (103).
Figure 6A:
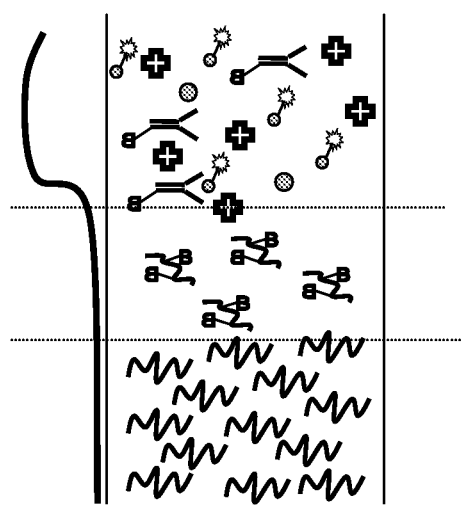
FIG. 6A represents a schematic of an initial state of a reaction chamber of three layers from top to bottom: a sample layer; a capture layer and a stacking layer, respectively. A sample layer can include any or all components on the left-hand side of the reaction represented in FIG. 3 with excess multivalent agent (e.g. neutravidin) in reaction buffer. A capture layer contains essentially uncharged capturable polymer (e.g. biotin-conjugated polymer) in reaction buffer. A stacking layer contains an essentially uncharged polymer (e.g. linear polyacrylamide). The gray trace shown on the left side of the chamber in each figure represents the detectable amounts of the Signal-Generating Antibody at each point.
Figure 6B:
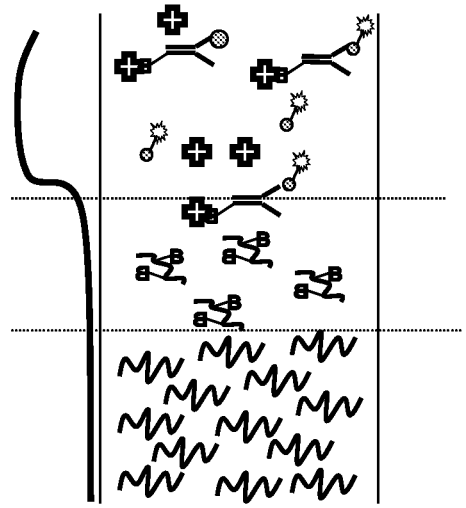
FIG. 6B represents a schematic of complexes capable of self assembly in an exemplary sample layer, represented by reactions represented in exemplary FIG. 3 and FIG. 4.
Figure 6C:
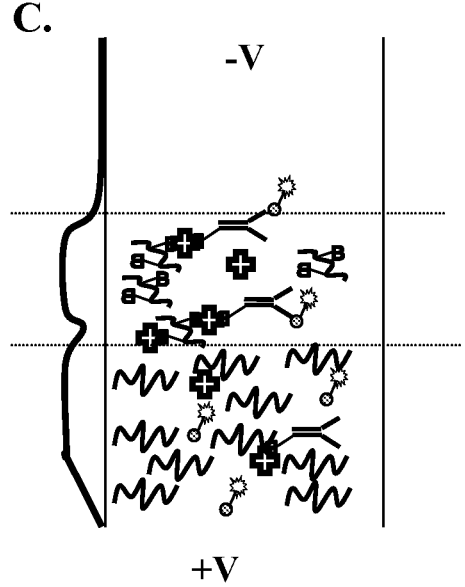
FIG. 6C represents a schematic of application of a voltage potential in the vertical direction, leading to the electrophoresis of all components into a capture layer, and formation of complexes represented by the reaction illustrated in FIG. 5.
Figure 6D:
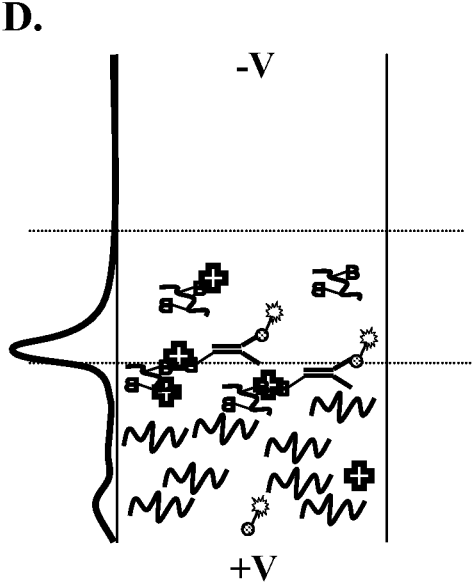
FIG. 6D represents a schematic of migration of all components from further application of the voltage potential, leading to the movement both into, and through, a stacking layer of all complexes not bound to the essentially uncharged capturable polymer (e.g. biotin-conjugated polymer), and concentration of bound complexes at the interface between the capture layer and the stacking layer.

The following steps represent exemplary methods and compositions for preparing a sample potentially containing a target molecule and analyzing the sample for the presence of and/or concentration of the target molecule. For example, a first step can include mixing and incubating a binding agent, a traceable agent-target molecule and the target molecule of interest (as a component of the sample to be assayed) together to allow the formation of complexes. Mixing these components can generate complexes including a binding agent which is bound to either a traceable agent-target molecule or to unlabeled target within the sample. In cases where the binding agent is multivalent, a binding agent may be bound to either or both a traceable agent-target molecule or unlabeled target. This is illustrated in FIG. 3.

In an alternative embodiment, a binding agent, a traceable agent-target molecule, a target molecule of interest (as a component of the sample to be assayed) can be mixed and incubated, and said components of the capture layer together to allow the formation of complexes, which consist of said binding agent which is bound to either said labeled target or to said unlabeled target within the sample, with the said binding agent also bound to the said polymers via the cognate binding agent of the polymer-associated capture agent.

Then an electrical potential can be applied across the electrophoresis chamber containing the mixture to separate complexes from the unbound traceable agent-target molecule, thus localizing these distinct groups of compounds containing traceable agent in time and space. In one embodiment, complexes will be localized at the interface between the capture layer and the stacking layer.

Measuring the traceable agent-target molecule associated with one or more complexes or unbound. In certain embodiments, presence and/or concentration of a target molecules in the sample can be measure through application of standard competitive assay kinetics. In one embodiment, analytical determination of the concentration of a target molecule can be performed. For example, overall signal(s) from one or more regions of the electrophoresis chamber in which complexes are expected to predominate, can be compared to the overall signal from regions of the electrophoresis chamber in which unbound traceable agent-target molecule is expected to predominate. Such a comparison can provide a normalization of the signal data, thus leading to a more accurate determination of the concentration of a target molecule in a sample.

Example 2

Calculation of Specific Mobility of Target and IgG-Target-Capture Polymer Complexes In one exemplary method, an electrophoretic mobility of an exemplary target protein, transferrin, was found to be approximately $9 \times 10^{-5}$ cm$^2$/s V in previous studies. From Equations 3C and 5, and using a molecular weight of 80 kilodaltons, an approximate charge can be calculated on each transferrin molecule of −3. IgG has a molecular weight of approximately 150 kilodaltons.

Because of the variable regions of the molecule, the charge can range from negative to slightly positive. One estimate of charge used in this example is −5. In one example, molecules of linear polyacrylamide (LPA) were used and were conjugated to multiple biotin molecules. In the presence of multivalent neutravidin, polymer networks comprised of LPA molecules cross-bound through biotin-neutravidin-biotin linkages form, and the molecular weight of these networks can reach into the many millions of daltons. The weight of the networks thus formed is considered in this example to be $10^7$ daltons. From Equation 2C, the mobility is inversely proportional to the cube root of the molecular weight.

From Equation 5, the electrophoretic mobility is proportional to the charge. Though ignoring such things as the difference in density between protein and LPA, and the hydration state of LPA, the uncertainty in the molecular weight of the LPA networks overwhelms these other effects, and so for the purposes of rough estimation, these effects will not be considered in this exemplary method. Based on the electrophoretic mobility of free transferrin, the electrophoretic mobility of the transferrin-antibody-LPA network complex can be represented by: $u=(9 \times 10^{-5})((-3+-5)/(-3))(80480+150+10,000)^{1/3}=2 \times 10^{-5}$ cm$^2$/s V.

The unbound transferrin moves approximately 4 to 5 times faster than the transferrin-antibody-LPA network complex. In certain examples, that the difference can be an order of magnitude greater than this.

In one exemplary method, using capillary electrophoresis voltages can be as high as 500 V/cm. One limitation is due to heat generation, which is proportional to the square of the applied voltage. In accordance with this exemplary method, by applying 100 V/cm, the free molecule moves at approximately 0.5 cm/min toward the anode (positive electrode), while the fully complexed transferrin moves at 0.1 cm/min in the same direction permitting clear separation of the free target molecules from those target molecules complexed.

Example 3

In one exemplary method, a target molecule of interest was the protein transferrin. In order to test certain embodiments disclosed herein, an antibody that specifically binds to human transferring was obtain and conjugated to a multivalent agent, biotin. The anti-transferrin antibody-biotin complex was then purified. Next, purified human transferrin was covalently labeled with fluorescein using commonly available techniques that still permit specific binding of the anti-transferrin antibody (e.g. rabbit derived antibody). The fluorescein linked transferrin and biotin conjugated antibody are mixed with an excess of neutravidin and with a sample that putatively contains unlabeled transferrin at a concentration of approximately 50 pM. The final mixture has 100 pM of the anti-transferrin antibody conjugated to biotin and 100 pM of the fluorescein linked transferrin. This mixture was incubated at 37° C. for 5 minutes.

Figure 8:
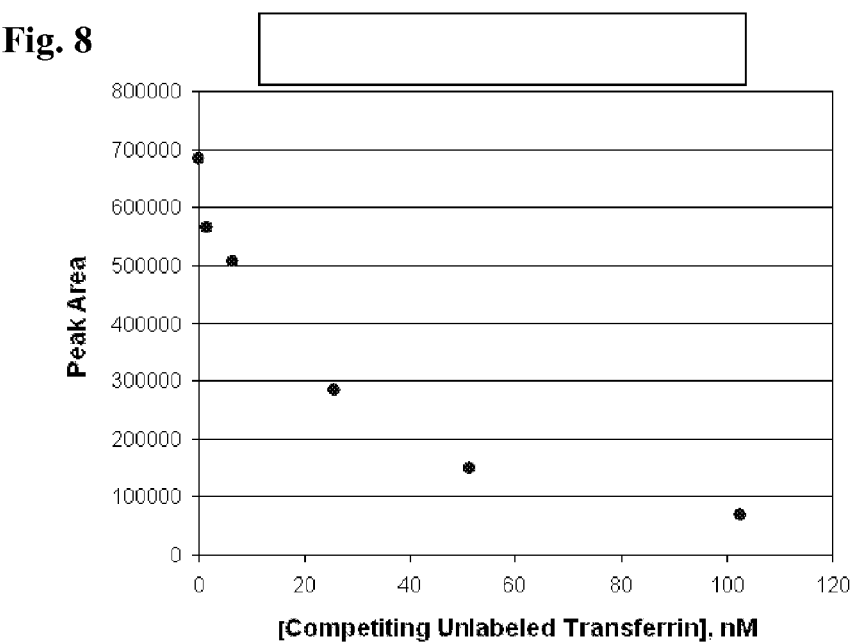
FIG. 8 represents exemplary plots of peak areas of the exemplary plots from FIG. 7A-7C, as well as, other unlabeled transferrin (target molecule) concentration between 0 and 102 nM, calculated at 10 minutes for the various concentrations. A typical competition curve is represented.
Figures 9A, 9B, 9C:
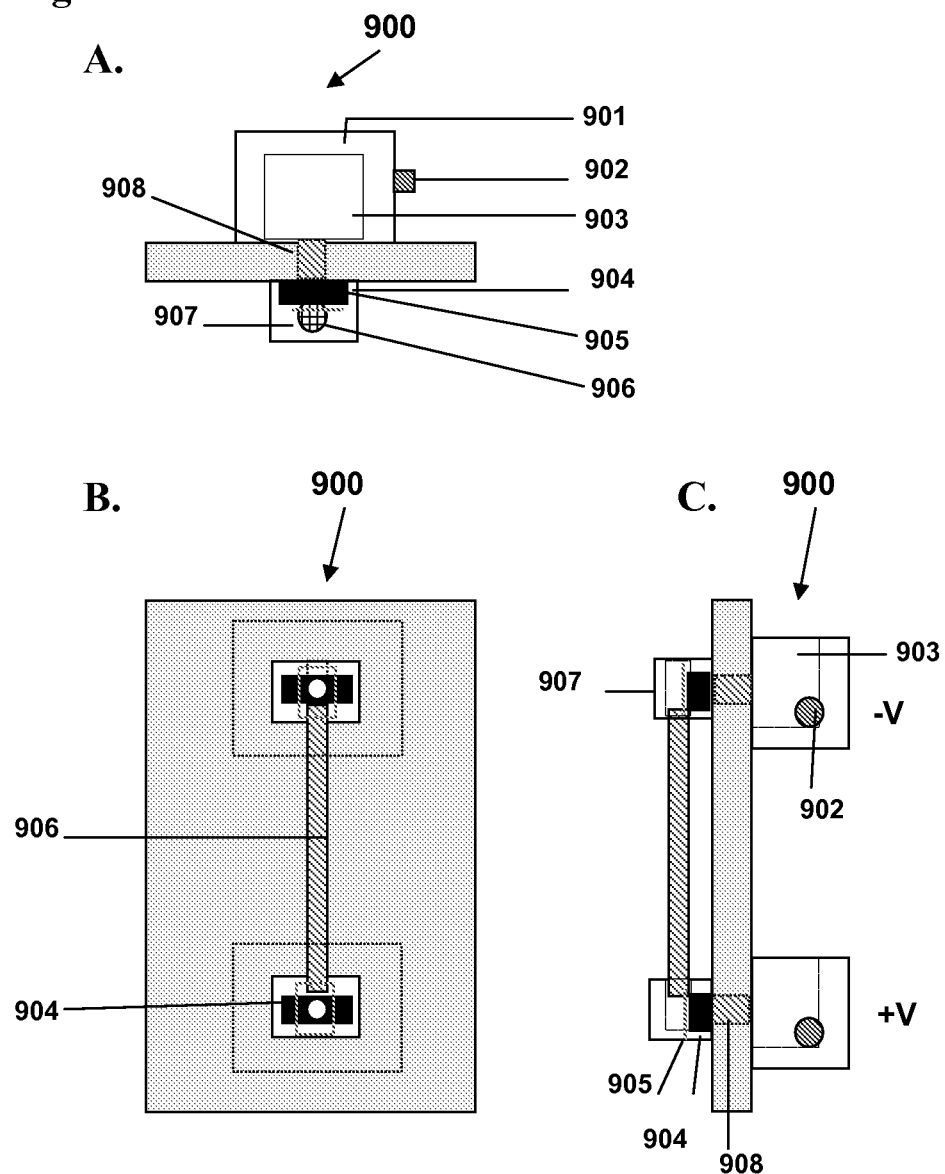
FIGS. 9A-9C represents an exemplary reaction chamber (900). 9A represents an exemplary top view of a reaction chamber including, but not limited to, (901) Platinum electrode, (902) Electrode terminal, (903) Buffer reservoir, (904) Silicon rubber gasket, (905) Dialysis membrane, (906) Quartz reaction channel, (907) and Channel bracket, (908) Voltage delivery channel between buffer reservoir and reaction channel. 9B represents an exemplary front view of a reaction chamber including, but not limited to, (906) Quartz reaction channel, and (904) Silicon rubber gasket. 9C represents an exemplary side view of a reaction chamber including, but not limited to, (907) Channel bracket, (903) Buffer reservoir, (902) Electrode terminal, (905) Dialysis membrane, (904) Silicon rubber gasket, (908) Voltage delivery channel between buffer reservoir, and reaction channel.
Figure 11:
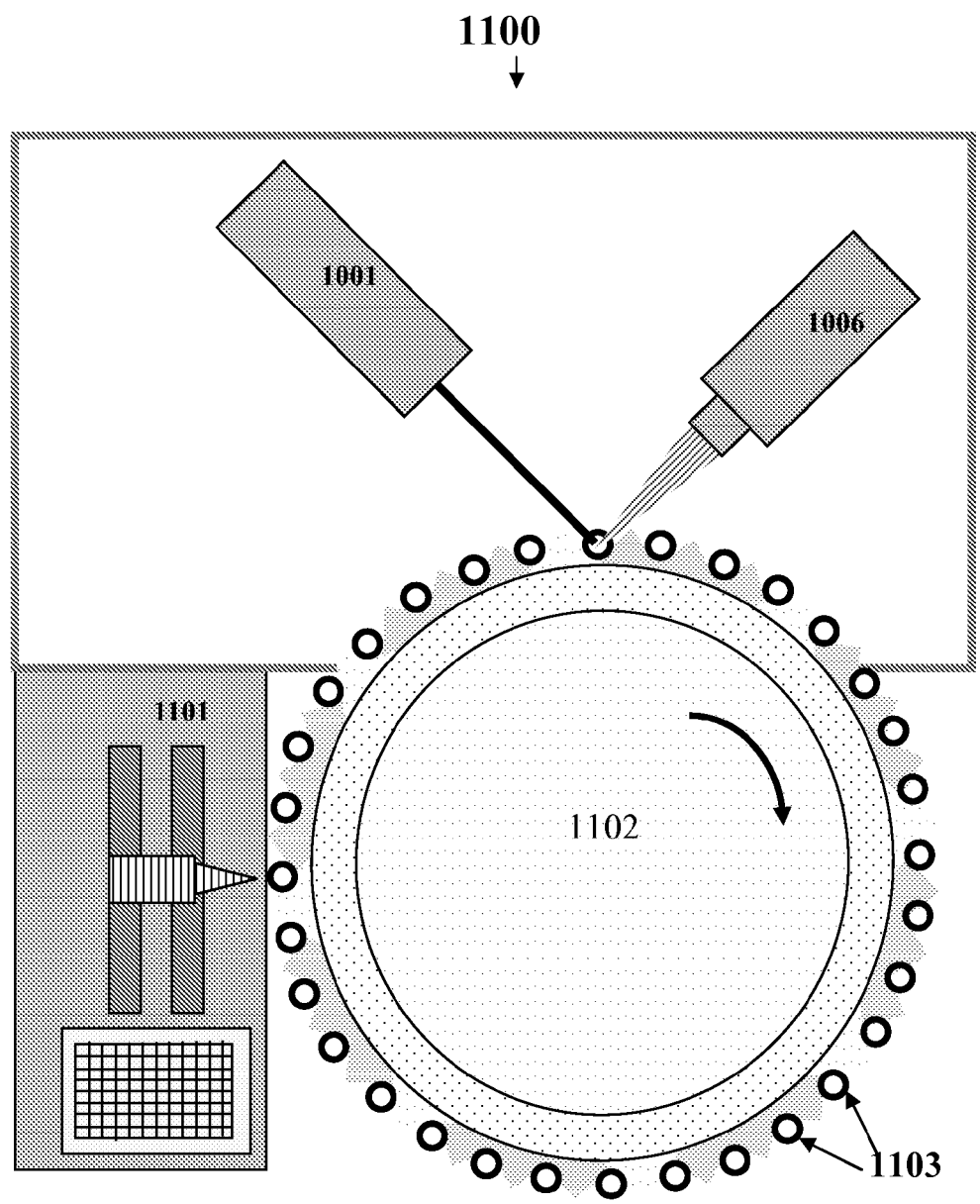
FIG. 11 represents an exemplary schematic of a system (1100) contemplated herein having multiple reaction chambers including, but not limited to, (1001) 473 nm continuous wave laser, (1006) CCD camera, (1101) Automated loading device, (1102) Rotating drum, and (1103) Reaction chambers.

The sample/antibody/labeled target mixture was injected into an electrophoresis cell, and a potential of 100 V/cm is applied for 5 minutes. For example, see FIGS. 6A-6D. The fluorescent signal in the capture layer can be measured for example, with a fluorescence detector. Optionally, the fluorescent signal of regions outside the capture layer may be measured, representing fluorescein linked transferrin that is not bound to antibody, due in part to the presence of unlabeled transferrin in the sample. A comparison of these two signals permits a more accurate estimation of target concentration in the sample. In another example, these steps can be repeated using samples putatively containing a variety of concentrations of a target molecule, for example 100 pM target molecule, 200 pM target molecule, or no target molecule The data can be tabulated and plotted on a graph, signals that are inversely proportional to the target concentration are utilized as illustrated in exemplary FIG. 8. Additionally, samples containing unknown quantities of target molecule such as transferring, may be analyzed following the above protocol. Using this example, transferrin concentration can be identified by extrapolation from a graph constructed from known transferrin concentration assay data (such as a "standard concentration curve" graph illustrated in FIG. 8).

Example 4

Figures 7A, 7B, 7C:
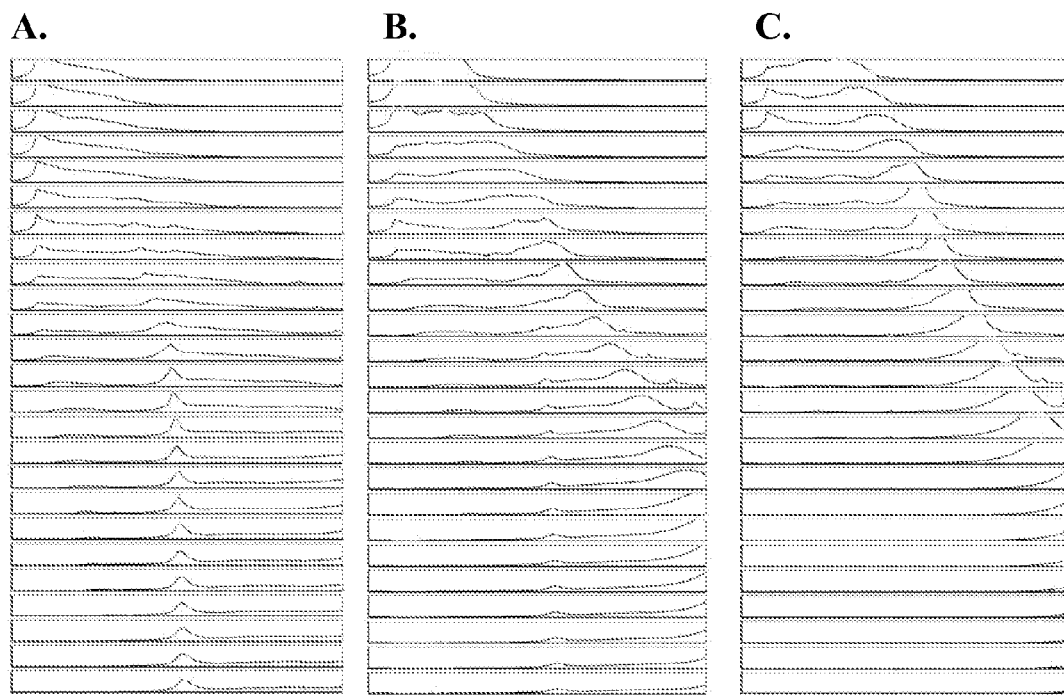
FIG. 7A represents exemplary plots of data from a dose-response experiment in which unlabeled transferrin (target molecule) in the sample competes with 8 nM FITC-labeled transferrin (traceable target molecule). These exemplary plots represent time-points at about 30 second intervals from top to bottom. The left side of each plot is closest to the cathode, thus most species migrate to the right.
FIG. 7B represents exemplary plots of data from a dose-response experiment in which unlabeled transferrin (target molecule) in the sample competes with 8 nM FITC-labeled transferrin (traceable target molecule). Conditions were the same as for FIG. 7A, except that 26 nM unlabeled transferrin was mixed into the sample layer along with all components from FIG. 7A.
FIG. 7C represents exemplary plots of data from a control run from a dose-response experiment in which unlabeled transferrin (target molecule) in the sample competes with 8 nM FITC-labeled transferrin (traceable target molecule). Conditions were the same as in FIG. 7A, except that the antibody (binding agent) was left out of the sample layer.

In one exemplary method, data from a proof-of-concept experiment is illustrated in FIGS. 7A-7C. As illustrated in FIGS. 7A-7C, neutravidin was used to demonstrate how a three-layer design functions to capture desired target molecules and focuses these targets into bands for detection. An electrophoresis cell for this assay was prepared, consisting of three layers: in the bottom ("stacking") layer was linear polyacrylamide in tris-acetate buffer and 7.5% glycerol; in the middle ("capture") layer was biotinylated dextran in tris-acetate buffer and 4% glycerol; and in the top ("sample") layer was FITC-labeled neutravidin in tris-acetate buffer. In the control run, the capture layer had no biotinylated dextran. The sample layer is located outside of the detection window, to the right in these plots. When a voltage was applied to the cell, the neutravidin migrated (to the left) into the capture layer, where it bound the biotinylated polymer, dramatically slowing its mobility. When the neutravidin-polymer complex reached the stacking layer, the presence of the linear polyacrylamide slowed the progress of the complexed neutravidin nearly to a standstill, focusing the band. Free neutravidin in the control run moved freely through both the capture and the stacking layers.

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for detecting the presence, absence or concentration of a target molecule in a sample comprising:
   (i) providing a sample containing a target molecule;
   (ii) exposing the sample to a traceable binding agent wherein the traceable binding agent specifically binds to the target molecule to form a target molecule-traceable binding agent complex;
   (iii) mixing the target molecule-traceable binding agent complex with unbound target molecule to provide a sample mixture;
   (iv) adding the mixture to a vertical stacked electrophoresis matrix, wherein the matrix consists of two or more phases increasing in density or viscosity from top to bottom, and one or more phases of the matrix have an uncharged polymer (p) capable of associating with a binding agent electrophoresed through the polymer containing phase(s); wherein
       (a) the vertical stacked electrophoresis matrix is provided in a vertically arranged vessel with a hydrodynamic radius of at least 0.5 mm;
       (b) at least one of said phases comprises a gradient of increasing density from 1.0 to 1.1 g/ml within the vertically arranged vessel;
       (c) the gradient comprises
           (1) a sample mixture layer of density 1.0 to 1.02 g/ml;
           (2) a capture layer of density from 1.002 to 1.05 g/ml; and
           (3) a stacking layer of density from 1.01 to 1.1 g/ml,
   wherein the stacking layer has a higher density than the capture layer, and the capture layer has a higher density than the sample layer; and
   detecting and measuring the presence, absence, or concentration of the target molecule-traceable binding agent complex by measuring or detecting relative amounts of the traceable binding agent in relation to the unbound target molecule to determine the presence, absence, or concentration of the target molecule in the sample.

2. The method of claim 1, wherein the traceable binding agent comprises a capturable binding agent.

3. The method of claim 2, wherein the capturable binding agent comprises one or more of a capturable antibody capable of binding to the target molecule, antigen-binding fragments of an antibody capable of binding to the target molecule, a biological receptor of the target molecule, a fragment of a biological receptor of the target molecule, a multivalent biotin binding agent, a tagged binding agent or a biotin-linked uncharged polymer.

4. The method of claim 1, wherein target molecule associated with traceable binding agent is measured relative to an unbound target molecule.

5. The method of claim 4, wherein target molecules associated with the traceable binding agent are electrophoretically separated from unbound target molecules.

6. The method of claim 1, wherein the target molecule is a protein or peptide.

7. The method of claim 1, wherein sample is loaded in the vessel and the vessel is selected from a tube, a channel or a container and the electrophoresis is performed in a gradient of increasing density and/or viscosity from top to bottom of the tube, channel or container, the gradient comprising at least three phases of increasing density or viscosity.

8. The method of claim 1, wherein said measuring of target molecule-traceable binding agent complexes and unbound target molecule provide a proportional and an inversely proportional signal to the target molecule concentration.

9. The method of claim 1, wherein the traceable binding agent is fluorescent, luminescent, chemiluminescent, a radionuclide, a metal ion or an enzyme that produces a fluorescent, luminescent, chemiluminescent or colored product.

10. The method of claim 1, wherein said detecting and measuring step further comprises:
receiving first data representing emission of a band, wherein the band comprises a target molecule-traceable binding agent complex in a sample mixture;
receiving second data representing a level of an unbound target molecule; and
comparing the first data to the second data to assess the presence, absence, or concentration of the target molecule in the sample mixture.

11. The method of claim 10, wherein said comparing the first data to the second data comprises determining a ratio of the first data and the second data.

12. The method of claim 10, wherein said comparing comprises generating a standard curve for each target molecule of interest in a sample mixture.

13. The method of claim 10, wherein said comparing further comprises comparing at least one intensity of the direct emission provided by bound target molecules compared to the inverse of unbound target molecule concentration.

14. The method of claim 10, wherein said comparing the first data to the second data to assess the presence, absence or concentration of a target molecule in a subject comprises:
recording emission signal intensities of a band of comprising a target molecule in the sample mixture in the capture layer as target emission signal intensity data;
analyzing the emission signal intensity data for each target molecule to determine the presence or concentration of the target molecule in the sample; and
electronically correlating the presence, absence, or concentration of the target molecule in the sample to provide data for health assessment of the subject providing the sample.

15. The method of claim 1, further comprising:
separating a sample mixture, the sample comprising a target molecule-traceable binding agent complex;
capturing emission signal intensity reading as recorded emission data from the target molecule-traceable binding agent complex using an emission reader;
receiving and analyzing the emission data received from the target molecule-traceable binding agent complex to determine the presence, absence or concentration of target molecule in the sample.

16. The method of claim 1, further comprising generating control data corresponding to at least one positive control sample of a target molecule of interest.

\* \* \* \* \*